(12) United States Patent
Katchinskiy et al.

(10) Patent No.: US 12,245,971 B2
(45) Date of Patent: Mar. 11, 2025

(54) SYSTEM AND METHOD FOR DETECTION OF FLOATERS

(71) Applicant: PULSEMEDICA CORP., Edmonton (CA)

(72) Inventors: Nir Katchinskiy, Edmonton (CA); Christopher Ceroici, Edmonton (CA); Iman Amini, Edmonton (CA); Geoffroy Rivet-Sabourin, Quebec (CA); Michael Brownell, Reno, NV (US); Eugene Shteyn, Cupertino, CA (US)

(73) Assignee: PULSEMEDICA CORP., Edmonton (CA)

( * ) Notice: Subject to any disclaimer, the term of this patent is extended or adjusted under 35 U.S.C. 154(b) by 0 days.

(21) Appl. No.: 18/642,465

(22) Filed: Apr. 22, 2024

(65) Prior Publication Data
US 2024/0269001 A1    Aug. 15, 2024

Related U.S. Application Data

(63) Continuation of application No. PCT/CA2022/051734, filed on Nov. 25, 2022.

(30) Foreign Application Priority Data

Nov. 30, 2021 (CA) .................. CA 3140678
May 6, 2022 (CA) .................. CA 3157811

(51) Int. Cl.
*A61F 9/008* (2006.01)
*A61B 3/10* (2006.01)
(Continued)

(52) U.S. Cl.
CPC .............. *A61F 9/008* (2013.01); *A61B 3/102* (2013.01); *G06T 7/0012* (2013.01); *G06T 7/521* (2017.01);
(Continued)

(58) Field of Classification Search
CPC .. A61F 9/008; A61F 9/00802; A61F 9/00819; A61F 2009/00874;
(Continued)

(56) References Cited

U.S. PATENT DOCUMENTS

2015/0305617 A1* 10/2015 Tachikawa ........... A61B 3/1225
351/246
2017/0360411 A1   12/2017 Rothberg et al.
(Continued)

FOREIGN PATENT DOCUMENTS

CA         3157811 A1    11/2023
KR    1020190130310 A1   11/2019
(Continued)

OTHER PUBLICATIONS

International Search Report and Written Opinion of corresponding PCT Application No. PCT/CA2022/051734; ISA/CA; Canadian Intellectual Property Office; Feb. 28, 2023; 16 pages.

*Primary Examiner* — Aaron F Roane
(74) *Attorney, Agent, or Firm* — Perkins Coie LLP

(57) ABSTRACT

Images of a patient's eye can be imaged and the images processed to detect and track floaters within the patient's eye. The floater detection and tracking can be used to identify characteristics of the floaters as well as possibly perform laser treatment of the floaters.

30 Claims, 23 Drawing Sheets

(51) Int. Cl.
    *G06T 7/00*           (2017.01)
    *G06T 7/521*         (2017.01)
    *G06T 7/70*           (2017.01)
    *G06V 10/764*       (2022.01)
    *A61N 5/06*           (2006.01)

(52) U.S. Cl.
    CPC .............. *G06T 7/70* (2017.01); *G06V 10/764* (2022.01); *A61F 2009/00874* (2013.01); *A61F 2009/00885* (2013.01); *A61N 2005/0643* (2013.01); *G06T 2207/10101* (2013.01); *G06T 2207/20081* (2013.01); *G06T 2207/30041* (2013.01); *G06T 2207/30242* (2013.01)

(58) Field of Classification Search
    CPC . A61F 2009/00885; G06T 7/521; G06T 7/70; G06T 7/0012; G06T 2207/10101; G06T 2207/20081; G06T 2207/20084; G06T 2207/30041; G06T 2207/30242; G06V 10/764; A61B 3/102; A61N 2005/0643

USPC ............................................................ 606/4
See application file for complete search history.

(56) References Cited

U.S. PATENT DOCUMENTS

| | | |
|---|---|---|
| 2020/0245960 A1 | 8/2020 | Richter et al. |
| 2021/0142487 A1* | 5/2021 | Xu ............................ G06T 7/70 |
| 2021/0186753 A1* | 6/2021 | Al-Qaisi ............. A61F 9/00736 |
| 2021/0224997 A1 | 7/2021 | Kushida et al. |

FOREIGN PATENT DOCUMENTS

| | | |
|---|---|---|
| WO | 2021029231 A1 | 2/2021 |
| WO | 2021069168 A1 | 4/2021 |
| WO | 2021069220 A1 | 4/2021 |
| WO | 2022077117 A1 | 4/2022 |
| WO | 2023065042 | 4/2023 |

\* cited by examiner

SYSTEM AND METHOD FOR DETECTION OF FLOATERS

RELATED APPLICATIONS

The current application is a bypass continuation of PCT Application No. PCT/CA2022/051734, filed Nov. 25, 2022, which claims priority to Canadian patent application 3,140,678 filed Nov. 30, 2121 and titled "SYSTEM AND METHOD FOR DETECTION OF FLOATERS," and Canadian patent application 3,157,811, filed May 6, 2022 entitled "SYSTEM AND METHODS FOR COMBINED REAL-TIME AND NON-REAL-TIME DATA PROCESSING," the entire content of which are incorporated herein by reference in its entirety.

TECHNICAL FIELD

The current disclosure relates to systems and methods for detecting and/or treating eye conditions and in particular to systems and methods related to the detection and or treatment of symptomatic vitreous opacities (SVOs), also known as floaters.

BACKGROUND

Symptomatic vitreous opacities (SVOs), commonly referred to as floaters, in a patient's eye can impact the patient's vision and/or comfort. Floaters are microscopic fibers that can tend to clump together within the vitreous of the eye that cast shadows over the patient's retina. Current treatment for floaters incudes removing the vitreous fluid that has the floaters and replacing it with a solution. New treatments can use lasers to breakup the debris within the vitreous. The lasers can be targeted at the debris by an ophthalmologist using a targeting laser. The manual targeting process can risk targeting non-floater elements within the patient's eye. Further, the manual targeting limits the minimum size of the floaters that can be targeted and treated using existing techniques.

An additional, alternative and or improved system and method for detection and/or the treatment of one or more eye conditions is desirable.

SUMMARY

In accordance with the present disclosure there is provided a system for use in treatment of floaters in an eye of a patient comprising: a first imaging system for capturing real-time images of the patient's eye; a laser treatment system for focusing and firing a treatment laser; and a controller for controlling the first imaging system and the laser treatment system, the controller configured to: detect a floater in an image captured by the first imaging system; track a position of the detected floater across images subsequently captured by the first imaging system; and focus the treatment laser of the laser treatment system at the tracked position of the detected floater for subsequent firing of treatment laser to treat the floater.

In a further embodiment of the system, the first imaging system comprises a scanning laser ophthalmoscopy imaging system.

In a further embodiment of the system, the treatment laser comprises a femtosecond laser.

In a further embodiment of the system, detecting the floater is done using a machine learning algorithm using large kernels for object detection.

In a further embodiment of the system, detecting the floater further comprises removing non-floater features of the eye from the image prior to using the machine learning algorithm.

In a further embodiment of the system, the non-floater features comprise veins in the eye.

In a further embodiment of the system, the system further comprises: a second imaging system for capturing real-time images of the patient's eye.

In a further embodiment of the system, the second imaging system comprises an optical coherence tomography (OCT) imaging system.

In a further embodiment of the system, a location within the eye that the OCT imaging system images is adjusted based on the tracked location of the floater.

In a further embodiment of the system, the OCT imaging system is used to determine a depth of the floater.

In a further embodiment of the system, tracking the position of the detected floater comprises stabilizing images subsequently captured by the first imaging system.

In a further embodiment of the system, the controller determines one or more of: a number of floaters; a surface area of floaters; a volume of floaters; a location of floaters; an opacity of floaters; a refractive index of floaters; a speed of movement of floaters; a direction of movement of floaters; and a concentration of floaters.

In a further embodiment of the system, detecting the floater uses a convolutional neural network (CNN) that takes as input a sequence of a number (M) of image frames captured by the first imaging system and determines a sequence of M floater detection masks corresponding to floater locations in each image frame of the input sequence.

In a further embodiment of the system, detecting the floater comprises: applying the CNN to a plurality of input sequences of M image frames, each of the plurality of input sequences including a frame of interest to provide a plurality of floater mask sequences each including a floater detection mask for the frame of interest; and summing the floater detection masks for the frame of interest from each of the plurality of floater mask sequences.

In a further embodiment of the system, detecting the floater further comprises: applying a threshold value to the summation of the floater detection masks.

In a further embodiment of the system, detecting the floater and tracking the position of the detected floater comprises: sending the image captured by the first imaging system to a remote server for detecting the floater in the image; buffer subsequently captured images from the first imaging system; receive a position of the floater detected in the image by the remote server; and track the position of the detected floater across the buffered images.

In a further embodiment of the system, the controller is further configured to predict a future position of the detected floater.

In a further embodiment of the system, the system further comprises a visible light imaging system.

In a further embodiment of the system, the system further comprises a gaze display.

In a further embodiment of the system, the gaze display is controlled in order to cause a patient to move their eye in a manner to affect a motion of a floater.

In a further embodiment of the system, the gaze display is controlled to determine a subjective impact of a floater on a patient's vision.

In a further embodiment of the system, focusing the treatment laser comprises: focusing the laser according to a treatment pattern determined for at least a portion of the detected floater.

In accordance with the present disclosure there is further provided a method for use in treatment of a floater, the method comprising: detecting a floater in a captured image; tracking a position of the detected floater across subsequently captured images; and focusing a treatment laser at the tracked position of the detected floater for subsequent firing of a treatment laser to treat the floater.

In a further embodiment of the method, detecting the floater is performed at a controller of an imaging system.

In a further embodiment of the method, detecting the floater is performed at remote server separate from a controller of an imaging system.

In a further embodiment of the method, the method further comprises buffering the subsequently captured images.

In a further embodiment of the method, the method further comprises capturing real-time images of the patient's eye using a second imaging system.

In a further embodiment of the method, the second imaging system comprises an optical coherence tomography (OCT) imaging system.

In a further embodiment of the method, adjusting a location within the eye that the OCT imaging system images based on the tracked location of the floater.

In a further embodiment of the method, the method further comprises using the OCT images to determine a depth of the floater.

In a further embodiment of the method, tracking the position of the detected floater comprises stabilizing images subsequently captured by the first imaging system.

In a further embodiment of the method, stabilizing the image comprises tracking retina movement in order to determine movement to be stabilized.

In a further embodiment of the method, the controller determines one or more of: a number of floaters; a surface area of floaters; a volume of floaters; a location of floaters; an opacity of floaters; a refractive index of floaters; a speed of movement of floaters; a direction of movement of floaters; and a concentration of floaters.

In a further embodiment of the method, detecting the floater uses a convolutional neural network (CNN) that takes as input a sequence of a number (M) of image frames captured by the first imaging system and determines a sequence of M floater detection masks corresponding to floater locations in each image frame of the input sequence.

In a further embodiment of the method, detecting the floater comprises: applying the CNN to a plurality of input sequences of M image frames, each of the plurality of input sequences including a frame of interest to provide a plurality of floater mask sequences each including a floater detection mask for the frame of interest; and summing the floater detection masks for the frame of interest from each of the plurality of floater mask sequences.

In a further embodiment of the method, detecting the floater further comprises: applying a threshold value to the summation of the floater detection masks.

In accordance with the present disclosure there is further provided a non-transitory computer readable medium having stored thereon instructions, which when executed by a processor of a computing device, configure the device to provide a method according to any of the methods described above.

BRIEF DESCRIPTION OF THE DRAWINGS

Further features and advantages of the present disclosure will become apparent from the following detailed description, taken in combination with the appended drawings, in which.

DETAILED DESCRIPTION

Figure 1:
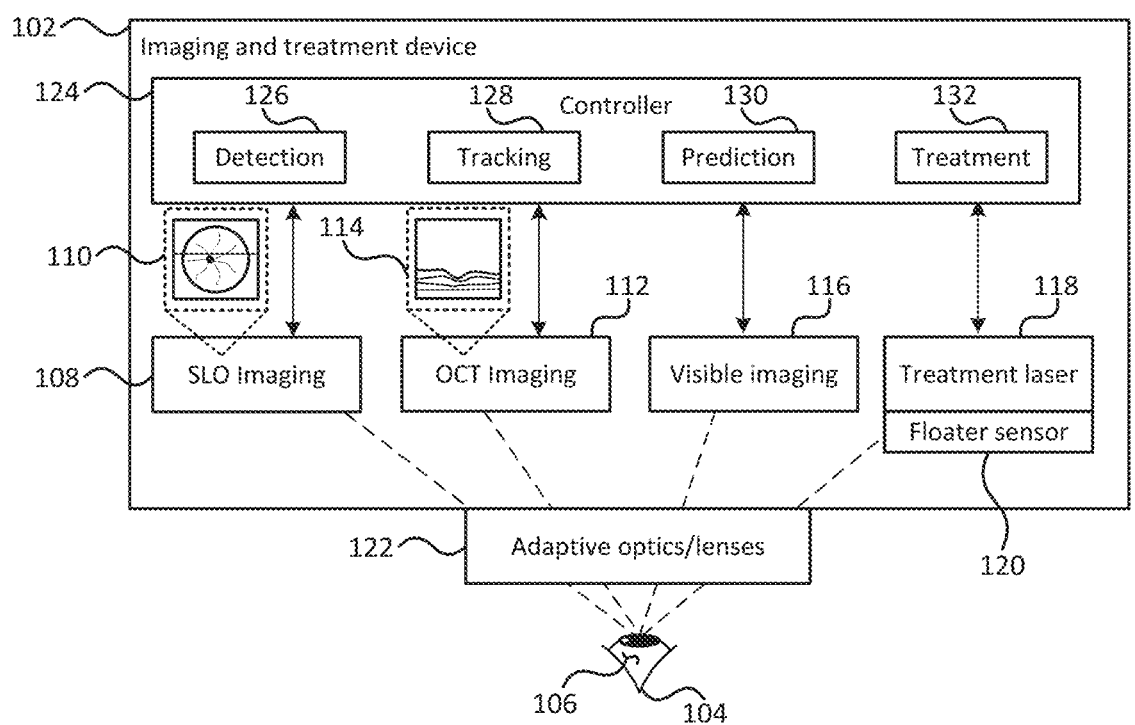
FIG. 1 depicts a system for the detection and treatment of floaters.

Symptomatic vitreous opacities (SVOs), commonly referred to as floaters, in a patient's eye can be detected using optical imaging and processing techniques. The detected SVOs can be detected and possibly tracked in real-time. The detection of the SVOs can be used in evaluating a patient's eye condition, determining treatment options, and/or treating the SVOs using a therapeutic laser. The treatment can include the ablation or removal or evaporation or liquification of the SVO, or portion thereof through a process of photo-ionization caused by one or more laser pulses.

With current imaging and targeting technology there is no direct feedback telling the doctor if the floater is within a safe treatment zone; i.e. if it's too close to the retina or the lens. Therefore, there is a need for a system that can image the floater within the eye and determine if it's safe to treat. Additionally, since the floater is moving independently of the eye, delivering 1000s of laser pulses onto the floater quickly is important. The shockwave generated by the laser pulses can result in the floater moving, as such, delivering pulses quickly before the floater has the chance to move is desirable. Further, with current technology, imaging the eye/floaters in 3D in real-time is not possible. Using OCT technology, it's possible to image a volume, however, acquiring a volume scan can take close to 1 full second at best. As such, having a methodology to image, detect and track, the eye and floaters in real-time is critical to ensure its position at all times and to determine if it's located within a safe treatment zone, and finally deliver automatically laser pulses quickly accurately and effectively to remove/reduce the size of the floater.

The detection and tracking of SVOs can be done in various ways as described further below using one or more different imaging devices. For example, a first imaging device, such as a scanning laser ophthalmoscopy (SLO) imaging device, can capture an image of the eye or portion of the eye within which a floater is visible. It will be appreciated that an SLO image may not capture an image of the actual SVO, but rather a shadow of the SVO on the retina. The image from the first imaging device can provide an X-Y image that allows a position of the floater to be partially determined, although the depth information about the position of the floater may not be determined by the first imaging device. The X-Y position/angle of laser scanning of the floater can be used to control an imaging location of a second imaging device capable of capturing depth information, such as an optical coherence tomography (OCT) imaging device. The images from the first and second imaging devices allows for the 3D location of floaters within the eye to be determined. The combination of multiple imaging devices which capture images in real-time can allow the 3D tracking of floaters to be done in real-time. The tracking information can be used for various purposes including for example measuring details of the floater(s) as well as possibly treating the floater(s) with a laser, such laser can be femtosecond laser with parameters of 1-20 uJ/pulse, 1030 nm central wavelength, repetition rates of 1 KHz-2 MHz, 100-300 fs per pulse.

FIG. 1 depicts a system for the treatment of floaters. The system comprises an imaging and treatment device 102 that can be used for imaging a patient's eye, depicted as eye 104. The patient's eye can have one or more floaters 106. The imaging and treatment device 102 is depicted a single device in FIG. 1, however it will be appreciated that the components can be provided in multiple separate devices. International patent application No. PCT/CA2021/051451 filed Oct. 15, 2021 entitled "OPHTHALMOLOGICAL IMAGING AND LASER DELIVERY DEVICE, SYSTEM AND METHODS," which is incorporated herein by reference in its entirety describes an imaging and treatment device that could be used as the imaging and treatment device 102. The imaging and treatment device 102 comprises an SLO imaging device 108 that can capture an X-Y image 110 of the patient's eye and an OCT imaging device 112 that captures a depth image 114 of the patient's eye. The OCT imaging device 112 can capture a depth 'slice' image at a particular horizontal location in the eye. Both of the imaging devices 108, 112 can capture multiple frames of images to provide real-time images, or videos of the patient's eye. The imaging components can further include a visible imager 116 that uses a 2D light sensor to capture a 2D image, which can use a non-coherent light source. As described in further detail below with reference to FIG. 2, the images captured from the imaging devices can be used in generating a graphical user interface (GUI).

Imaging and treatment device 102 can also include a treatment laser 118 that can be targeted and fired at a particular location within the patient's eye, such as at a floater. The laser can be one of various known treatment lasers, including for example a femtosecond laser. Other lasers can be used including for example nanosecond lasers, picosecond lasers, microsecond lasers, millisecond lasers, or continuous wave (cw) lasers. The SLO imaging device 108, the OCT imaging device 110 and the treatment laser 118 can be calibrated so that all of the coordinate systems of devices are optically aligned or co-registered such that a location in one of the device's coordinate system can be aligned with the same location in the coordinate system of the other devices. The optical alignment can be achieved by adjusting the optical path of different imaging and/or treatment devices so that they are physically aligned with each other. The co-registration can be achieved using software techniques to adjust images or coordinates of different optical systems so that corresponding locations are co-located. The optical alignment and/or the co-registration can be achieved in various ways including those described in PCT Publication WO 2122/077117, filed Oct. 15, 2121 and entitled "OPTHALMOLOGICAL IMAGING AND LASER DELIVERY DEVICE, SYSTEM, AND METHODS," the entire contents of which are incorporated herein by reference in their entirety.

Although not depicted in detail in FIG. 1, it will be appreciated that each of the imaging devices 108, 112, 116 as well as the treatment laser 118 will include an optical pathway and other components, such as light sources, sensors, etc. The optical pathways of the imaging devices and treatment later can include at least a portion of the optical pathways that are common to all of the devices. For example, the last portion of the optical pathway before the patient's eye can be common to all of the devices.

The imaging system can include adaptive optics and/or lenses 122 within the optical pathway of one or more of the imaging and treatment components. As depicted in FIG. 1, the adaptive optics/lenses can be located so that the optical pathway of all of the imaging components pass through the adaptive optics/lenses; however, the adaptive optics/lenses can be located such that they are within the optical pathway of particular imaging components. The adaptive optics/lenses can be used to tune interactions between the laser and tissue through beam modifications. The adaptive optics/lenses can change one or more characteristics of the laser light such as the wavefront and/or the polarization. The wavefront can be modified to be, for example, a Gaussian or non-Gaussian wavefront.

The polarization of the laser of one or more of the imaging and treatment components can be adjusted to provide differing polarization, such as a radial polarization. A radial polarization can be useful in providing a smaller focal spot size of a laser such as a femtosecond laser used as a treatment laser. Further, the radial polarization can provide a force to the center of the beam that can tend to move or keep debris in a particular location.

The imaging and treatment components 108, 112, 116 and 118, as well as the adaptive optics/lenses 122 can be controlled by a controller 124 that is configured to provide various functionality including patient's head position/motion detection and tracking, eye location/motion detection and tracking, retina tracking, floater detection functionality 126, floater tracking functionality 128, floater path prediction functionality 130 and floater treatment functionality 132. The floater detecting functionality, path prediction functionality and the floater tracking functionality can be provided by the same or similar functionality or can be provided by separate functionality.

For example, the floater detection functionality 126 can use image processing techniques to detect floaters within the SLO images. Floater and more specifically floater shadow detection can be difficult using current techniques. Current object detection techniques perform well when detecting object with relative sharp edges. A machine-learning based object detection technique can use kernels for feature extraction/detection with a relatively small kernel size, such as 3×3 or 4×4. The floaters in the captured SLO images are shadows of the actual floaters and typically do not include sharp edges. In order to improve the floater detection, the object detection can be modified to use relatively large kernel sizes of for example, 8×8, 16×16, 32×32, and larger.

Additionally, floater detection can be further complicated by other features within the image. For example, features such as veins within the eye can make the floater detection difficult. It is possible to identify the non-floater features within the images and then remove or mask those features from within the images prior to attempting to detect the floaters. The non-floater features can be detected using various image processing techniques including machine learning image classification techniques and/or object detection techniques.

It will be appreciated that there is various different movements of the patient that complicate detecting a floater. For example, the floater moves within the vitreous humour of a patient's eye, which moves within the patient's head, which can move. The current systems can decouple the movement, for example by tracking the movement of the retina in order to stabilize, possibly through software processing, the images of the patient's eye. Stabilizing the captured images can make the identification of the floater easier. For example, in a video of the patient's eye that is not stabilized, the image of the eye including stationary structures such as the veins, macula, etc. will appear to move which makes it difficult to identify the floaters which are also moving. When the video of the eye is stabilized so that the stationary structures remain stationary, identification of the moving floaters can be easier.

The floater path prediction functionality 130 can predict the future position of one or more of the floaters. For example, the floater tracking can be used to predict floater locations in future frames, with the predicted locations. The predicted locations can be used to speed detection/tracking and the treatment of the floaters. The velocity and future positions of floaters can be predicted using a technique combining the fluid dynamics of floater motion in the vitreous with machine learning forecasting. Since eye motion will affect floater motion, an input to the machine learning forecaster can include the motion of the eyeball as measured by an imaging technique such as SLO or other techniques for retina tracking.

Although not depicted in FIG. 1 a calibration device can be provided that models an eye and includes a one or more floaters within the calibration device. The calibration device can be used to calibrate the device 102 and ensure that it is operating properly. The floaters within the calibration device can be of known size, and location within the eye that can be imaged and used to calibrate dimensions of the imaging systems.

The controller 124 can further include floater tracking functionality 128. Regardless of the particular details on the image processing used to detect floaters, once detected the floaters can be tracked across subsequently captured images. The tracking can be done using conventional image processing or tracking techniques such as optical flow. Additionally or alternatively, the tracking can use the same or similar functionality as the object detection. Conventional techniques can be modified to use additional information from previous tracking. For example, the floater tracking can be used to predict floater locations in future frames, with the predicted locations used to speed detection/tracking of the floaters.

The tracking functionality 128 can track the floater's X-Y position/angular scan required to capture the floater across the SLO images. The OCT image, or images can be used to track the depth, or Z, position information of the floater. The tracked X-Y position of the floater can be used to control the location that is imaged by the OCT imaging device. The OCT imaging device can provide a depth window that is insufficient to image the entire depth of the patient's eye and as such multiple OCT images can need to be captured covering different depths in order to detect the depth of the floater. Once detected, the depth of the floater can be tracked and predicted. The predicted floater depth location can be used to control, at least the initial, imaging depth of the OCT images to increase the likelihood that the floater is captured by the OCT images. Further, multiple OCT images of adjacent depth slices can be captured to capture depth information for the entire volume of the floater.

As described above, the SLO and OCT imaging devices 108, 112 can be used to detect and track one or more floaters in both the X-Y image plane of the SLO imaging device as well as the X-Z, and/or Y-Z or depth, image plane of the OCT imaging device. It will be appreciated that reference to the X-Y and X-Z image planes are used only for explanation and other relative axes and coordinate systems could be used to provide information about the physical location of the floater. The tracked floater location can be used by treatment functionality 132 of the controller to target the treatment laser 118 at an appropriate location for treating the floater with the laser. Prior to firing the treatment laser, it is possible for the treatment functionality 132 to verify the safety of the possible treatment location. For example, if the floater is in front of and close to the retina, it can be determined that firing the treatment laser pose too big of a risk for hitting the retina and so cannot fire the laser. Additionally or alternatively, it is possible for the treatment functionality to adjust laser parameters based on a safety level of the treatment location. For example, if there are no other features close to the treatment location, it can be possible to increase the treatment laser power level, or firing duration of the laser without causing risk to the patient's eye.

It will be appreciated that the imaging, detection, treatment and tracking of floaters can be performed repeatedly. That is, the detection process can be continually performed in order to detect floaters. Similarly the tracking process can be performed constantly to continually track floaters. Alternatively, the detection process can be performed periodically to detect all floaters and begin tracking each of the detected floaters. The periodic detection can be used to update the tracking and/or detect new floaters. If the detection is performed periodically, the detection can be performed during the floater treatment which can break up the floater into additional smaller floaters.

The detection and tracking of the SVO, or more particularly the shadow of the SVO on the retina using a first imaging modality capturing and X-Y image of the eye, such as an SLO image or fundus image, can be used to control the scan path of a second imaging modality capturing depth, or Z-axis, information such as an OCT modality. The quality of the imaging can depend upon the use of the images. For example, if the captured images are only used for imaging of the eye and possible subsequent characterization of one or more conditions of the patient, the imaging does not need to be done in real time. In contrast, if the imaging is performed as part of a treatment process, the imaging can need to be completed in real-time or near real-time.

For imaging only mode, an OCT volume scan that is slightly larger than the shadow, taking into account a predicted trajectory of the floater can be captured. Image post-processing can be performed in order to remove motion artifacts due to motion of the floater while obtaining a 3D volume, since the OCT imaging of the volume takes a finite amount of time, such as approximately 1 second.

Further, although the second imaging modality that captures depth information is described as an OCT imaging modality, other techniques can be used. For example, it can be possible to capture depth information of a floater using the SLO imaging device by sweeping the focus of the SLO device through the depth of the vitreous in order to image the SVO itself. This can be used to provide real-time imaging in the X-Y as well as depth information of the SVO using only the SLO imaging device. The depth information can be determined based on a focusing depth of the SLO device when the SVO is captured and in focus. Further, the SLO imaging can be performed using the femtosecond treatment laser as the light source in order to provide 2-photon or multi-photon imaging of the eye. In the detection side, it can be possible to reject the wavelengths of the femto source and only accept harmonics of the source. For example, the femto second laser source can be a 1030 nm laser source, and so the second harmonic would be 515 nm. The optical path of the SLO imaging device can include a bandpass filter for the 515 nm harmonic. Floaters are made of collagen, which can act as a crystal and creates second harmonics that can be captured and visualized by the SLO. The interaction between collagen and the laser source, such as the femto second laser, can result in result in different harmonics and as such, the second harmonic signal resulting from the femtosecond laser source can be relatively strong for a floater compared to the vitreous itself.

In addition to the $2^{nd}$ harmonics, the collagen of floaters interacting with the treatment laser, or possibly imaging lasers, can result in a red or blue shift. The resulting red or blue shifted light can be filtered and captured by an appropriate sensor. The sensor can be the SLO imaging device or possibly a floater imaging device 120 that can capture the red or blue shifted light in order to image floaters.

Figure 2:
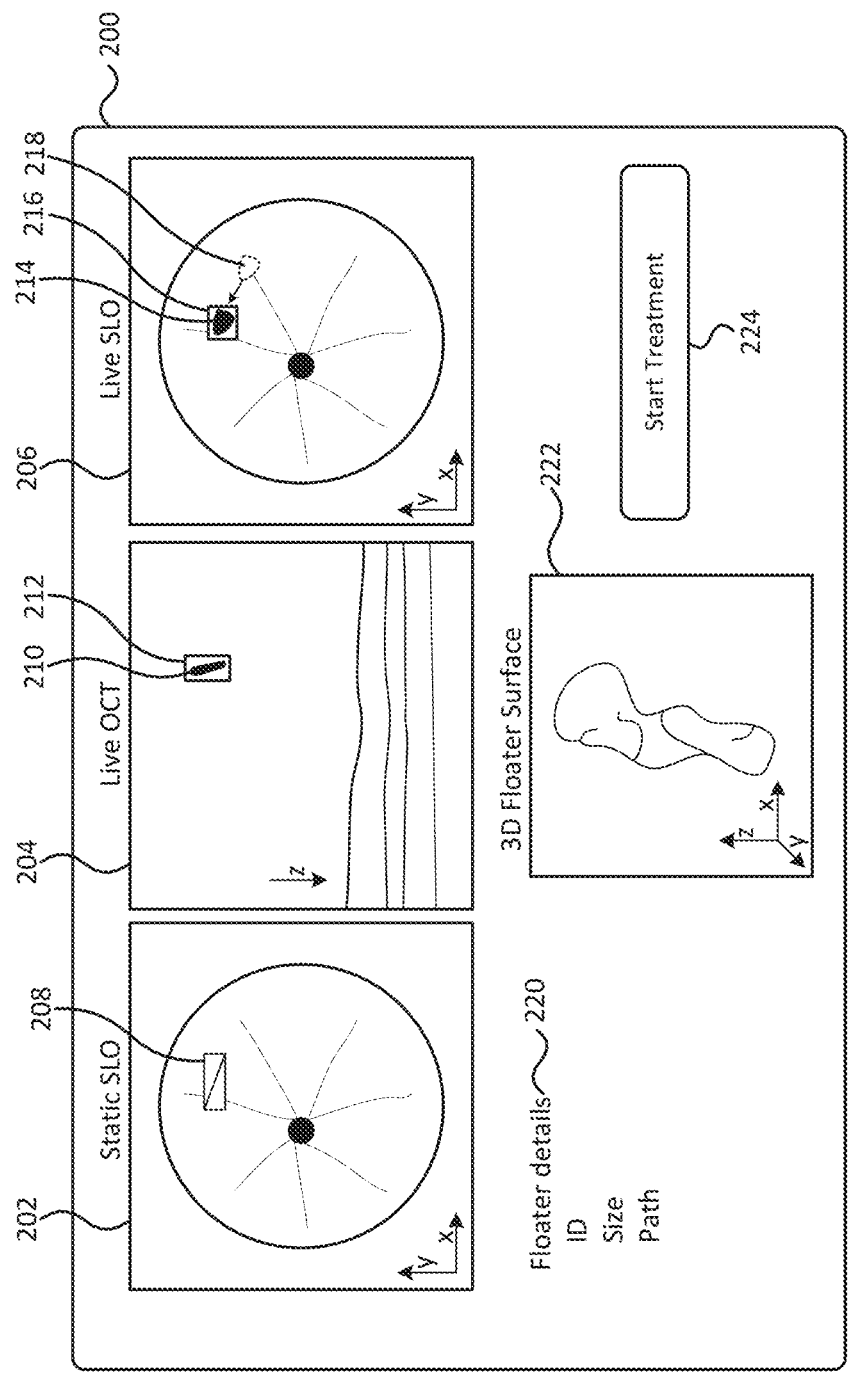
FIG. 2 depicts an illustrative graphical user interface for use in the detection and treatment of floaters.

FIG. 2 depicts an illustrative graphical user interface for use in the detection and possible treatment of floaters. As depicted in FIG. 2, the GUI 200 can present various information to a user, including for example a static SLO image 202 of the patient which provides an image of the eye in the X-Y plane. Although described as an SLO image, the static image 202 can be a fundus image captured with techniques other than SLO. The static image 202 can be from a previously captured image of the patient's eye. In addition to the static image 202, the GUI 200 can also provide live video or images captured from different imaging modalities. Two different imaging modalities are depicted in FIG. 2, which include OCT images 204 and a live SLO 206. The OCT image can provide depth information in the Z axis capture along on or more scan lines, referred to as B-scans.

The static SLO image 202 can include additional information such as an indication 208 of where the scan line or path along which the OCT scan image 204 is captured. Additional information can be presented on the static image such as locations of features of the eye including possibly veins, unsafe regions, etc. as well as other locations such as treatment locations, and unsafe treatment regions.

The live OCT image 204 can display one or more SVOs 210. The SVOs can be highlighted in various ways including such as by placing a bounding box around the SVOs. Additional information can also be overlaid on the OCT image. In addition to the live OCT image, the GUI 200 can also provide a live SLO image, or fundus image 206. The live SLO image can overlay the images with additional information. The live SLO image 206 can show the SVO 214, or the shadow of the SVO on the retina. Additional information can be overlaid on the live SLO image 206 including for example a bounding box 216 or other highlighting feature of the SVO. Further, a path (direction and speed) 218 of the SVO can be highlighted.

The GUI 200 can provide additional information about one or more of the SVOs including details of the floater such as an identifier, a size, path or trajectory, and other relevant information. Additionally a 3D representation of the SVO 222 can be provided. The 3D representation can be generated from multiple image frame and/or images, including both SLO and OCT images. The GUI can allow interaction with one or more of the elements. As an example, one or more of the displayed SVOs can be selected and the details, possibly including a generated 3D representation of the selected SVO can be presented. Additionally, the GUI 200 can further include one or more elements allowing the user to interact and perform one or more actions such as starting a treatment 224 for treating one or more of the detected and tracked SVOs.

Although not depicted in FIG. 2, the GUI can present various different information to the user. For example, the safe zones, that is the areas, regions or zones within the eye that are safe for treatment by the laser, can be shown or highlighted on both the SLO and volumetric or OCT depiction. The safe zone can be provided as an outline of the safe zone, or can be presented as a coloured overlay. Additionally, or alternatively, SVOs and/or other features can be highlighted, for example by overlaying the SVOs and/or features in a colour when they are in, or out, of the safe zones. The information presented can also include information about the floaters and/or characteristics of one or more floaters, for example a number of floaters, surface area of individual floaters, total surface area of all floaters, volume of individual floaters, total volume of all floaters, locations of floaters, opacity of floaters, refractive index of floaters, speed of movement of floaters, direction of movement of floaters, concentration of floaters, etc.

Additionally, although the GUI depicted in FIG. 2 shows a 3D representation of a single floater, it can be possible to provide a 3D visualization of the patient's eye, including one or more of the floaters that are being tracked. The 3D representation can allow the user to get a better understanding of whether or not a particular floater is in a location that is safe for treatment.

It will be appreciated that different professionals can prefer different information to be displayed. The GUI can allow customization with regard to what and where particular information is displayed. Further, the GUI, or other functionality that the GUI interacts with, can provide functionality allowing the professional to interact with the displayed information. For example, the imaging system can use a high-resolution OCT imaging device and the GUI can provide functionality allowing the professional to zoom in and zoom out on the live OCT image. The GUI can zoom-in on a high resolution OCT image by enlarging a portion of the OCT image that is displayed. When the OCT image is captured in high resolution, portions can be enlarged, or zoomed in on without significantly degrading the image quality that is displayed. The GUI can provide controls for zooming in and out, such as a "+" and "−" button. Additionally or alternatively, the zoom functionality can be controlled by other inputs such as keyboard keys or combinations of keys and/or mouse buttons. The zoomed in display can help to provide a professional with a more detailed view of one or more SVOs, which can be desirable in evaluating a patient's SVOs and establishing a treatment plan Zoom in/out with and OCT system can also be achieved by controlling the modes of the OCT laser source and detector and digitizer. For example, by changing the wavelength bandwidth of the laser source resolution can be controlled. However, by increasing the wavelength bandwidth more sampling needs to be performed to retain the same scan rate. Therefore the scan rate needs to be controlled in order to satisfy the limitation of the digitizer inside the system. In addition, by increasing the OCT imaging window more samples need to be acquired at the same time. Therefore, either wavelength bandwidth can be reduced or scan speed can be reduced. As an example, an OCT system can come with a few pre-configured imaging modes. For example, Mode 1 (imaging for treatment): large imaging window (e.g. 10 mm in water) low resolution and low scan speed of 100 khz. Mode 2 (treatment mode): short window (e.g. 4 mm in water) high resolution and high scan speed of 240 khz). Mode 3 (imaging only): large imaging window (e.g. 10 mm in water) high resolution and high speed of 240 khz.

Zoom in and Zoom out can also be performed on the SLO by controlling the scan pattern of the SLO galvo-resonant scanner.

Figure 3:
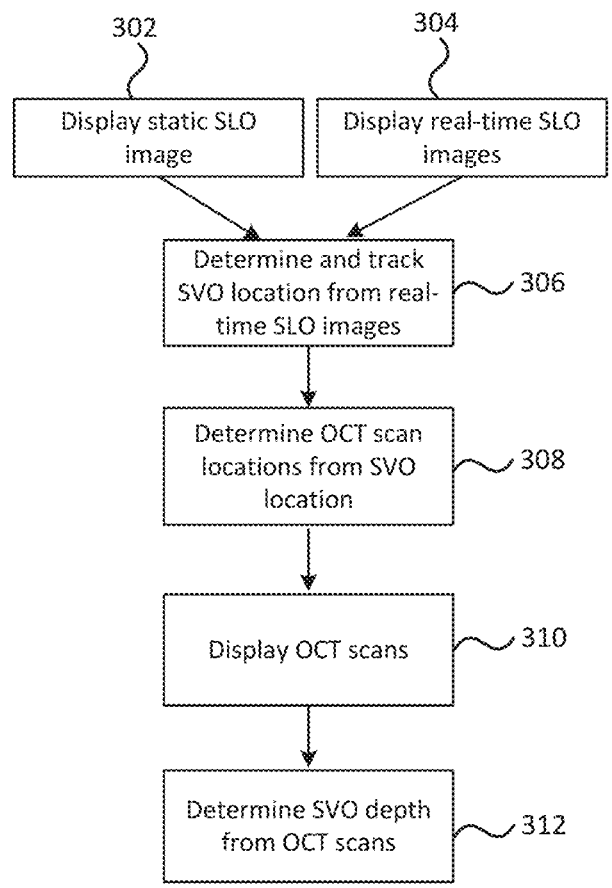
FIG. 3 depicts a method for the detection and display of floaters.

FIG. 3 depicts a method for the detection and display of floaters. The method 300 can be performed at a device such as that depicted in FIG. 1 or can be provided by other devices with varying components. The method 300 generates and displays a static SLO, or fundus, image of the patient's eye (302). Generating the static image can include generating an overlay of information on the static image. In addition to generating the static image for display, real-time SLO images are generated and displayed (304). The real-time SLO, or fundus, images are used to determine and track SVO locations from real-time SLO images (306) and the determined SVO locations can then be used to determine OCT scan locations/patterns (308). The particular OCT scans can be based also on characteristics of the SVO in the SLO image. For example, darker areas of the SVO in the SLO can be considered more important and as such more scans can be performed in the darker areas of the SLO image. The OCT scans can be displayed (310) and used to obtain depth information of the SVO (312). The GUI displayed by the method 300 can display the OCT scan paths on the static SLO image and can highlight the SVOs in both the live OCT scans and SLO images. The GUI can be used to display SVOs as they are tracked. The SVOs can be treated by a laser to break up the SVOs. The SVOs can be scanned with the OCT in such a way to produce a 3D volumetric representation.

Figure 4:
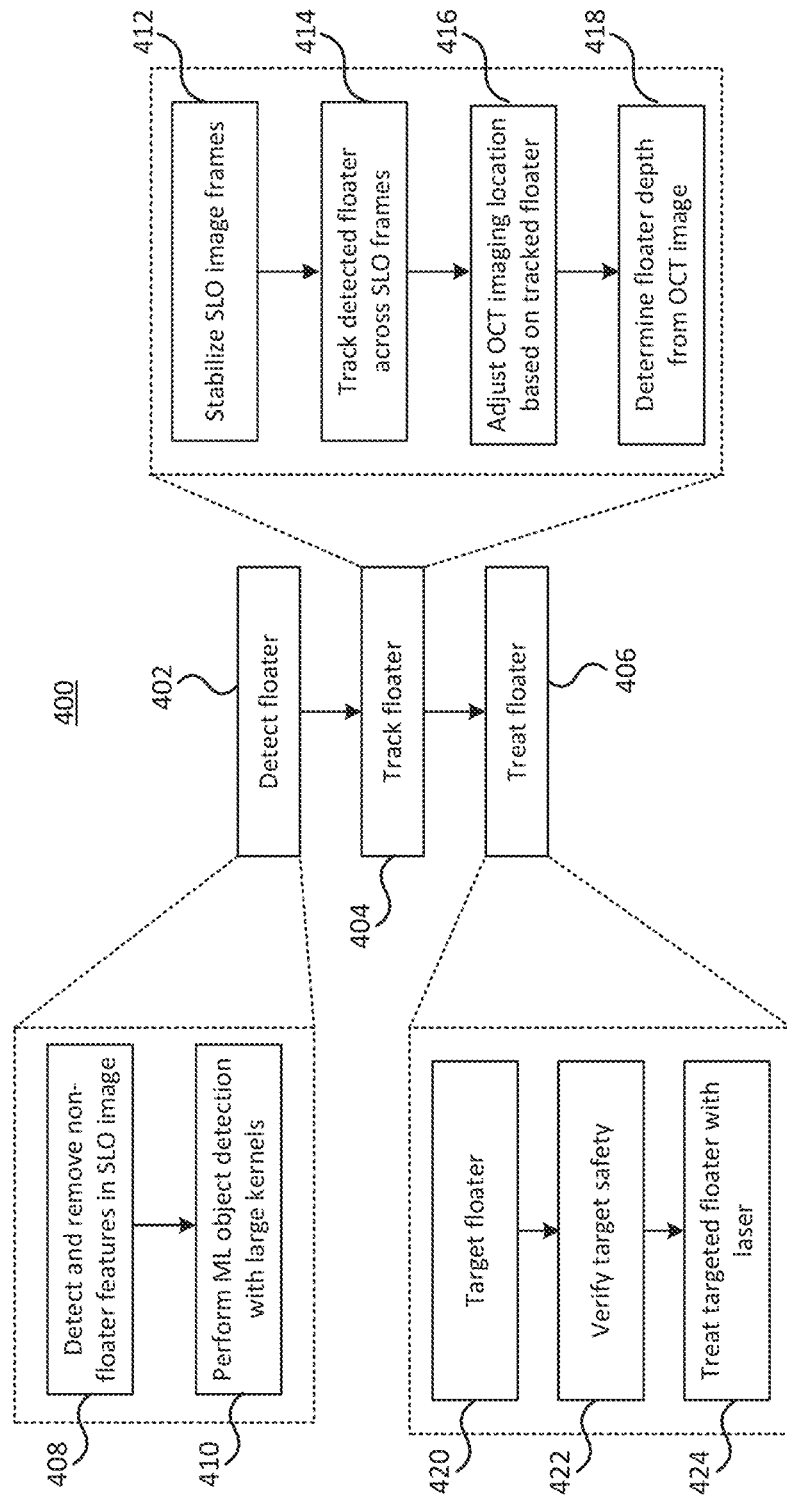
FIG. 4 depicts a method for targeting a laser for use in the treatment of floaters.

FIG. 4 depicts a method for targeting a laser for use in the treatment of floaters. The method 400 begins with detecting a floater (402) in an image. The image captures a plane of the patient's eye, and can be for example a SLO image or a regular camera image. The floater detection from the SLO image identifies a location of the floater but does not include the depth information. Once the floater location is detected (402), its position can be tracked across multiple images (404). The floater tracking (404) can provide the location, including depth information, of the floaters. The floater tracking can use images captured using both the first imaging device (i.e. the SLO imaging device) and the second imaging device (i.e. the OCT imaging device). With the floater location tracked, the floater can be treated (406) by targeting a laser at the tracked location.

The floater detection (402) can be performed in various ways. For example, as depicted in FIG. 4, the detection can begin with detecting and removing, or masking, non-floater features in the SLO image (408). The non-floater features can be for example veins or other natural structures of the eyes. The non-floater features can be detected using imaging recognition functionality. The image with the non-floater features removed or masked, can be processed using machine learning (ML) object detection for detecting the floaters (410). The non-floater features can be identified by utilizing fast retina tracking such as that as described in PCT patent application PCT/CA2022/051556 filed Oct. 21, 2022 entitled "FAST RETINA TRACKING" the entire contents of which is incorporated herein by reference in its entirety, where the background retina images are corrected using the fast tracker information in order to "make" the retina 'stationary'. Since the floater moves independently of the retina it can be identified by the detection algorithm.

The ML object detection can use various ML models including deep learning models, neural networks and other model architectures. The models can be trained using a wide range of training processes. The object detection can be unsupervised, semi-supervised or fully-supervised. The floater detection can be based on existing ML object detection processes, which typically rely on relatively small kernels for feature detection/identification. The ML object detection can be modified to use a relatively large kernel size, such as for example 16×16, 32×32 or larger. The larger kernel size improves the detecting of floaters or floater shadows which do not have well defined edges in the images.

Once the initial location of a floater is detected in the SLO image, its position can be tracked across multiple frames of the SLO images. In addition to tracking the position of the floater in the SLO images, the tracking can also be performed on the OCT images in order to track the depth of the floater. The tracking can be performed in various ways. As depicted, the tracking can begin with stabilizing SLO image frames (412). The stabilization can be done by registering stationary features within the eye across different frames. Additionally or alternatively, the stabilization can be based on eye movement determined by tracking the retina or features of the eye. The retina tracking can be done using various techniques including that described in PCT patent application PCT/CA2022/051556 filed Oct. 21, 2022 entitled "FAST RETINA TRACKING" the entire contents of which are incorporated herein by reference in their entirety. The floater can be tracked across different frames of the stabilized images (414) using known techniques such as optical flow. Further, the tracking can make use of previous tracking information, for example to predict a likely location of the floater in a current frame in order to accelerate the tracking process. With the location of the floater tracked in the SLO image frames, the OCT imaging location can be adjusted to capture depth strips at the floater location (416). With the OCT imaging location adjusted, the OCT imaging can capture one or more OCT images which can be processed to determine the depth of the floater (418). The OCT imaging device can only be able to capture the depth slice images over a particular window depth size, which may not cover the entire depth of the patient's eye. Accordingly, a single OCT image may not capture the floater and as such the depth window can be adjusted until the floater is captured. The OCT imaging device can allow the depth of focus to be adjusted in order to change the window depth until the floater is detected in the OCT image. The depth of the floater can be used as a starting depth for subsequent OCT imaging.

With the depth and position of the floater tracked, the floater can be treated (406). Although the floater can be treated in various ways, as depicted, the treatment can be performed using a laser. The treatment includes targeting, including focusing, the treatment laser at the tracked position/depth of the floater (420). The safety of firing the laser at the target location can be verified (422) and assuming that the treatment location is safe, the laser can be fired at the floater (424) to break it up/ablate it/liquify it/vaporize it/ablate it/photoionize it. Verifying the safety of the target can include determining the proximity to other features of the eye that could be damaged by the laser. If the features are within a path of the laser, or within a threshold distance of the path of the laser, the location can be deemed unsafe for treatment. As will be appreciated, floaters are moving within the eye and as such the tracking can continue until the floater is determined to be in a 'safe' location for treatment. Verifying the safety of the treatment location can consider the treatment location relative to other features of the eye as well as possibly other factors such as the power and duration of the treatment laser. In addition, a dynamic safety zone needs to be considered. Parts within the eye can sustain laser pulses spaced with minimum application time and/or sustain a maximum number of laser pulses. Since floaters move, due to delivery of laser pulses towards certain regions within the eye, if the floater moves back into those regions, those regions can be considered either permanently or temporarily unsafe.

Figure 5:
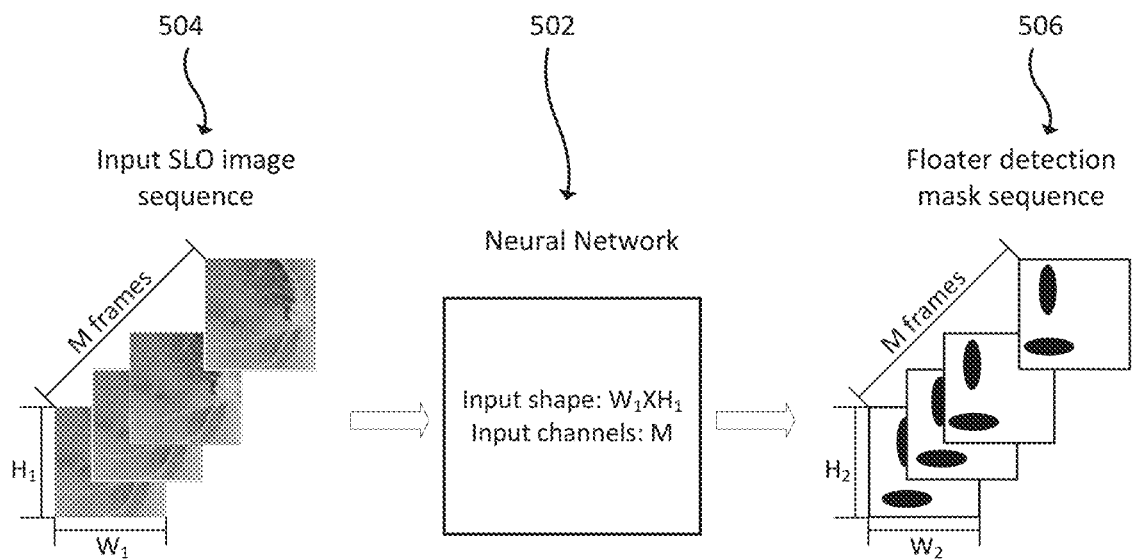
FIG. 5 depicts a floater detection process.

FIG. 5 depicts a floater detection process. The process can be implemented in hardware such as by a FPGA (Field programmable gate array) or ASIC (application specific integrated circuit) or by software executed on hardware such as a FPGA, ASIC, processor, microprocessor, GPU (graphics processing unit), DSP (digital signal processor). Etc. The process 500 uses a convolutional neural network (CNN) 502 to process a sequence of SLO images 504. The CNN 502 outputs a sequence of masks 506 providing detected locations of floaters. This system can be trained in a fully-supervised manner in which the training ground truth targets consist of hand annotated SLO images where floaters have been annotated. The floaters within the captured images are typically out of focus, and more so the closer they are to the front of the eye, with very blurry edges and typically just vague gradients providing low contrast. Conventional image tracking and object detection typically relies either on (i) landmarks, which are areas of high contrast to track over time or (ii) edges. In the detection of floaters, the areas of interest have very low contrast, even compared to other features in the SLO such as the optic disk, and also have no defined edges. Accordingly, the conventional image tracking processes tend to fail when detecting/tracking floaters.

The detection process 500 uses a convolutional neural network 502 in a configuration similar to U-Net. Rather than using as inputs the individual color channels of an image such as RGB, the input to the CNN 502 comprises an image with resolution W1×H1 with M channels, where M is the number of frames in the SLO sequence. The input can therefore be considered the sequence of frames of one channel each as captured by the SLO imaging device. The output comprises of segmentation masks 506 showing the locations of floaters. The output masks also have M channels, each with a resolution of W2×H2 which need not be the same as the input resolution W1×H1.

The CNN model can be trained on a collection of SLO image sequence/videos in which floaters have been labeled. The kernels of the convolutional layers can have larger sizes than typically found in CNNs such as 8×8, 16×16, 32×32 to accommodate the detection of larger feature sizes specific to floaters.

Figure 6:
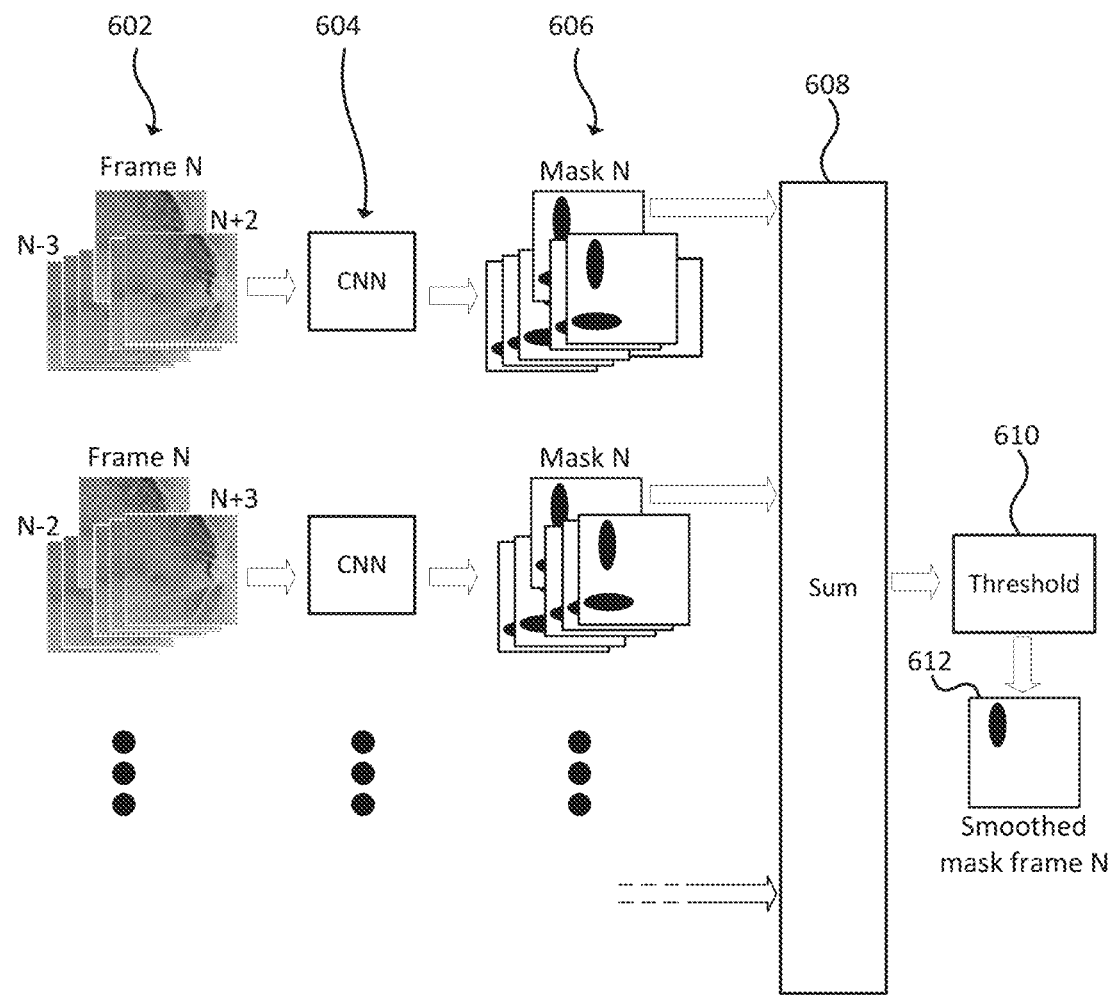
FIG. 6 depicts a further floater detection process.

FIG. 6 depicts a further floater detection process. To increase accuracy of the floater detection process 500 described above, as well as to have an adjustable "sensitivity" metric, the process 600 uses multiple image sequences 602 to identify floaters in a single frame. For example, to detect floaters on frame N=20, with a sequence length of M=6, the floater detection on frame 20 can be performed with a sequence of frames consisting of frames 17 to 22, frame sequences 18 to 23, etc. Each of these sequences will produce floater mask predictions for frame 20 using CNNs 604, which can be the same as that described above in FIG. 5. By predicting across some or all of the frame sequences which include frame 20, a number of prediction mask sequences 606 is obtained with each sequence including a mask for the frame of interest, i.e. frame 20. The masks of the frame of interest can then be added together 608. If, for example, 5 sequences of images were used, resulting in 5 different prediction masks for frame 20, with each mask consisting of values ranging from 0 to 1, the sum of the masks will range from 0 to 5. A sensitivity threshold 610 can then be specified between 0 and 5 to fine tune performance parameters such as false positive detection and output the smoothed floater mask for the frame of interest 612. Alternatively, the multiple masks can be compounded using methods such as multiplication, or a neural network.

The machine learning based floater detection can be combined with classical tracking methods. After detecting the floater using a ML model as described above, the predicted location can be passed to a classical image processing-based approach for object tracking such as optical flow. The predicted motion of the classical image processing-based object tracker can be used to limit the search area for subsequent ML-based detection of the floater. Additionally or alternatively, after the classical image processing-based object tracker is activated on a detected floater, the ML-based detection method can periodically be activated to re-estimate the location of the floater and ensure continued tracking accuracy.

Figure 7:
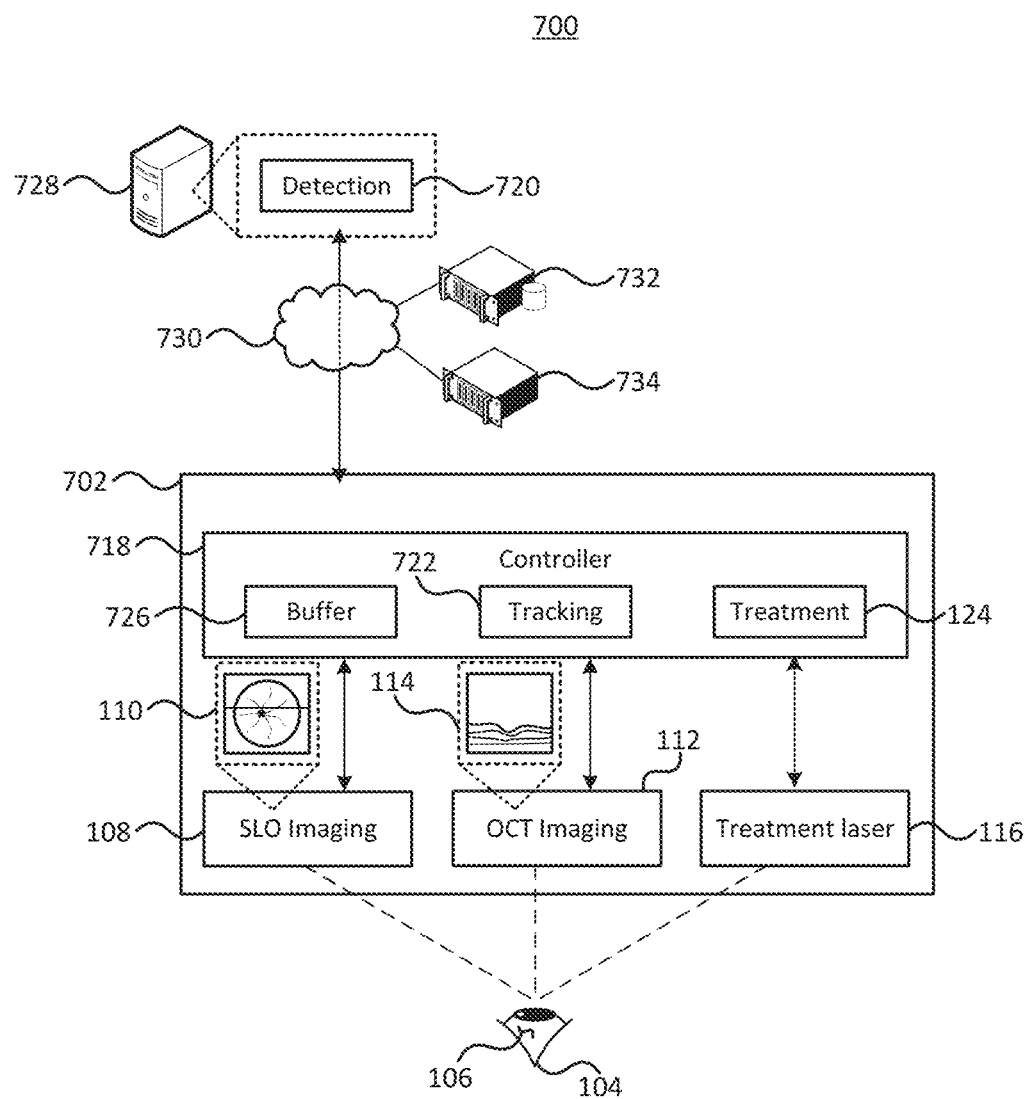
FIG. 7 depicts a distributed system for the treatment of floaters.

FIG. 7 depicts a distributed system for the treatment of floaters. It is noted that not all possible components of the distributed system are depicted in FIG. 7. For example, the device 702 may include additional components such as optical imaging components, additional sensors, adaptive optics/lenses or other components. The floater imaging and treatment device described above has been described as having a single controller that detects, tracks and treats the floaters. The image processing techniques can require a large amount of processing to perform quickly enough to make the real-time tracking and treating of floaters possible and practical. The system 700 can use a remote server, or other remote processing device to provide the required processing requirements of the image processing. While the remote processing can be faster, or make possible improved image processing, the additional communication and possibly processing time, make it difficult to provide real-time detection and tracking of floaters. The system 700 described above makes use of an image buffer to make the detection/tracking possible. The system 700 is similar to the floater imaging and treatment device 102 described above, and as such similar elements are not described in further detail.

The system 700 can send the captured images to a remote server 728 via a communication network 730 for processing. The remote server 728 can provide image detection functionality 720, which can perform the floater detection and returns the results back to the imaging and treatment device 702. There can be a delay in receiving the detected floater location information from the remote server, which would make the detected location unsuitable for use in subsequent tracking in the most recent images. In order to deal with the delay, the device uses an image buffer that can temporarily store the images captured subsequent to sending the images to the remote server for detection. Upon receiving the detection results from the remote server 728, the buffered images are used to track the floater from detected location to the current image frames. The controller 718 can use tracking functionality 722 that can be substantially similar to the tracking 122 described above; however the tracking can be performed on the buffered images. The tracking can be performed relatively quickly so that the tracking across the buffered images can be 'fast-forwarded', or performed faster than real-time, to the current frames and the tracking continued in real-time. Such a 'fast-forwarding' process is described in Canadian patent application 3,157,811, filed May 6, 2022 entitled "SYSTEM AND METHODS FOR COMBINED REAL-TIME AND NON-REAL-TIME DATA PROCESSING," the entire contents of which are incorporated herein by reference in their entirety.

The imaging and treatment device 702, and/or the remote server 728 can be in communication with one or more other servers, which can provide storage for image and patient data 732 as well as $3^{rd}$ party services that can be integrated with the other functionality.

Although the above has described the detection as being done at a remote server, a similar buffering and fast-forward tracking can be used even if the detection is not performed at a remote server. That is, if the detection process performed takes a length of time that makes it difficult or impossible to use the detected location as a starting point for tracking in the current images, the same process of buffering images and then fast-forwarding the tracking of the detected location across the buffered images can be applied.

Figure 8:
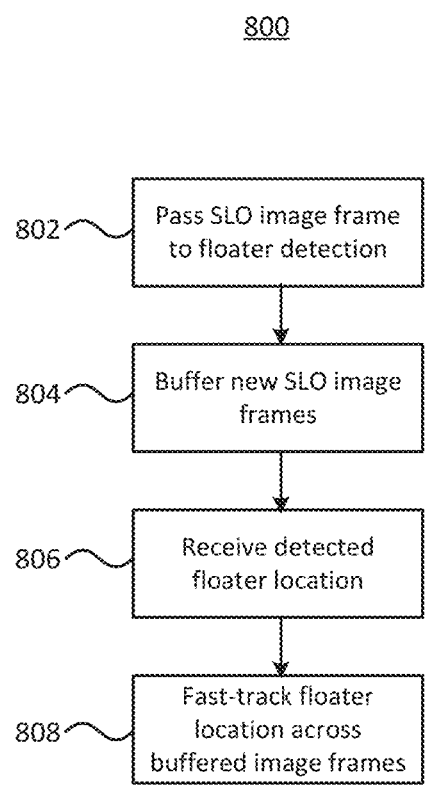
FIG. 8 depicts a further method for targeting a laser for use in the treatment of floaters.

FIG. 8 depicts a further method for targeting a laser for use in the treatment of floaters. The method 800 can be used to track floater locations from an initial detected location using a detection process that can take a length of time that makes using the detected location as an initial tracking location difficult. The method 800 passes an initial image, such as an SLO image, to floater detection functionality (802). The floater detection functionality can be performed locally or remotely. While the initial floater location is determined, newly captured SLO image frames are buffered (804). The detected floater location is received (806) and then used as the initial location for tracking the floater location across the buffered images (808). The tracking of the floaters across the buffered images can be performed relatively quickly, allowing the tracking across the buffered images to catch up to the currently captured images. Such a process can be performed using a technique as described in Canadian patent application 3,157,811, filed May 6, 2022 entitled "SYSTEM AND METHODS FOR COMBINED REAL-TIME AND NON-REAL-TIME DATA PROCESSING."

Figure 9:
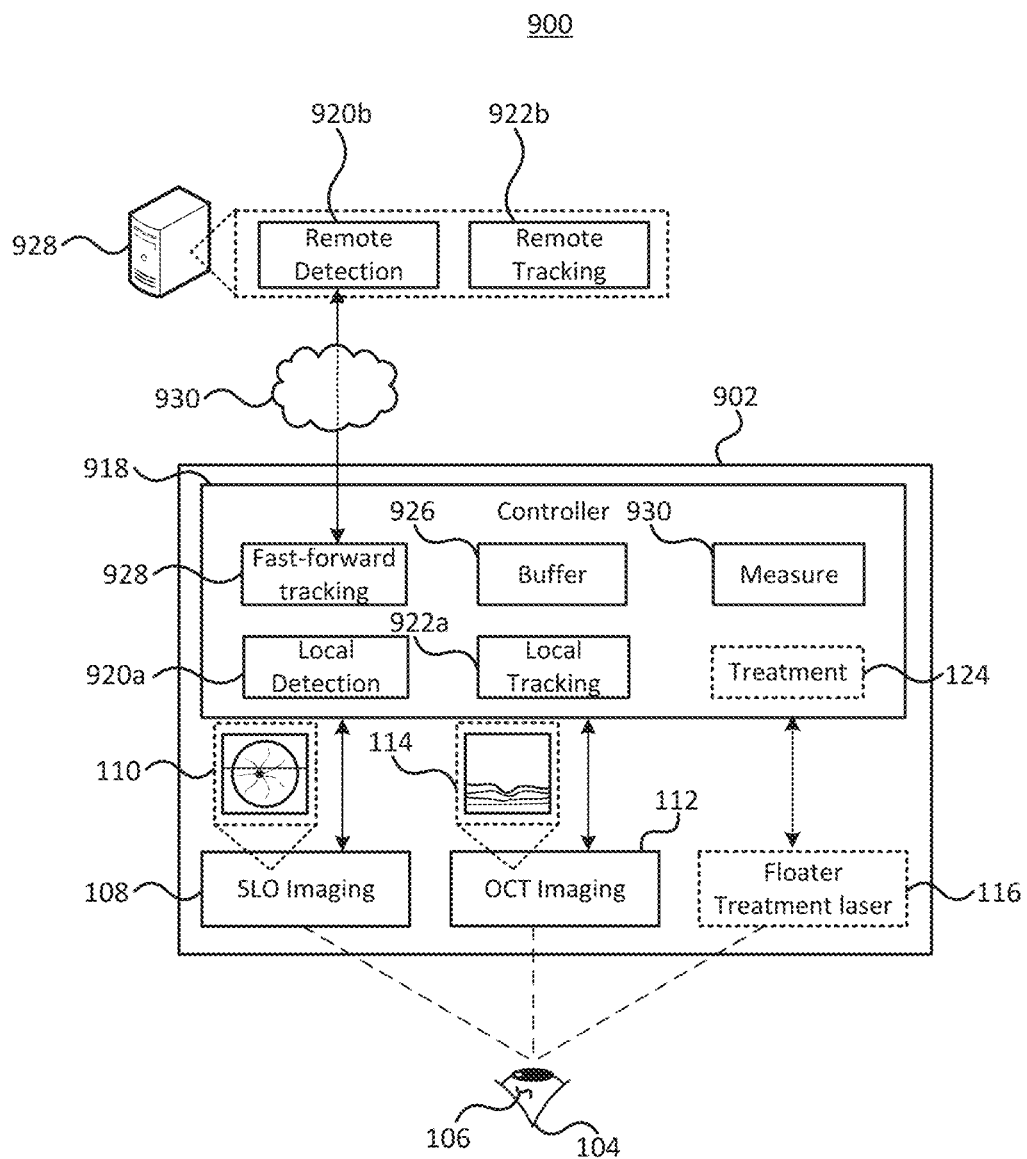
FIG. 9 depicts a distributed system for the detection of floaters.

FIG. 9 depicts a system for the detection of floaters. It is noted that not all possible components of the distributed system are depicted in FIG. 9. For example, the device 902 may include additional components such as optical imaging components, additional sensors, adaptive optics/lenses or other components. The system 900 is similar to those described with reference to FIGS. 1 and 5. Similar features and functionality will not be described again in detail. The system 900 can include an imaging and treatment device 902 that includes the first (i.e. SLO) imaging device 108, and the second (i.e. OCT) imaging device 112; however, unlike the devices of FIGS. 1 and 7, the device 902 can omit a floater treatment laser 116, and similarly the controller 918 can omit the treatment functionality 124. The controller can include local detection functionality 920a and possibly local tracking functionality 922a that perform floater detection and tracking respectively. The local detection and local tracking can work in conjunction with, or be replaced by, remote detection functionality 920b, and remote tracking functionality 922b provided by a remote server 928 in communication with the device 902 via a communication network 930. It will be appreciated that although the server is remote from the device, it does not need to be physically distant from the device 902. The controller can also include an image frame buffer 926 and a fast-forward tracking functionality 928 to track a floater from a detected location across buffered images in the buffer 926.

While the above has described tracking floaters and using the tracked location for targeting a treatment laser, it is possible to use the tracked floater information for other purposes. For example, the floater images and locations can be processed in order to identify and/or determine characteristics about the floater(s). This information can include for example a number of floaters, surface area of individual floaters, total surface area of all floaters, volume of individual floaters, total volume of all floaters, locations of floaters, opacity of floaters, refractive index of floaters, speed of movement of floaters, direction of movement of floaters, concentration of floaters, etc. These characteristics can be used for various purposes including for example determining a severity of the patient's floater condition, determining a an appropriate treatment referral pathway, determining possible likelihood of successfully treating floaters with lasers, also to train machine learning models for treatment and diagnostic purposes, etc.

Figure 10A:
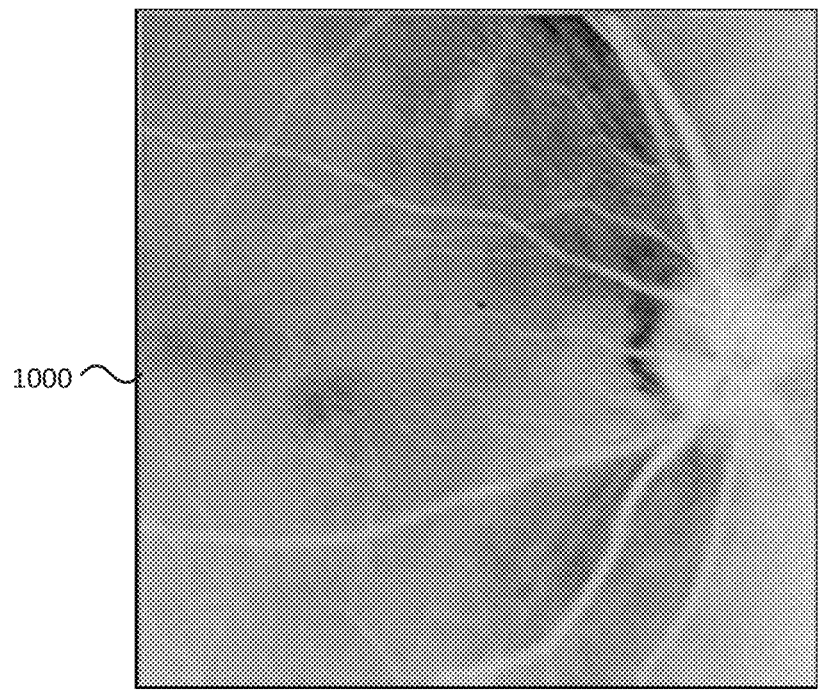
FIG. 10A depicts an image of an eye with a floater.
Figure 10B:
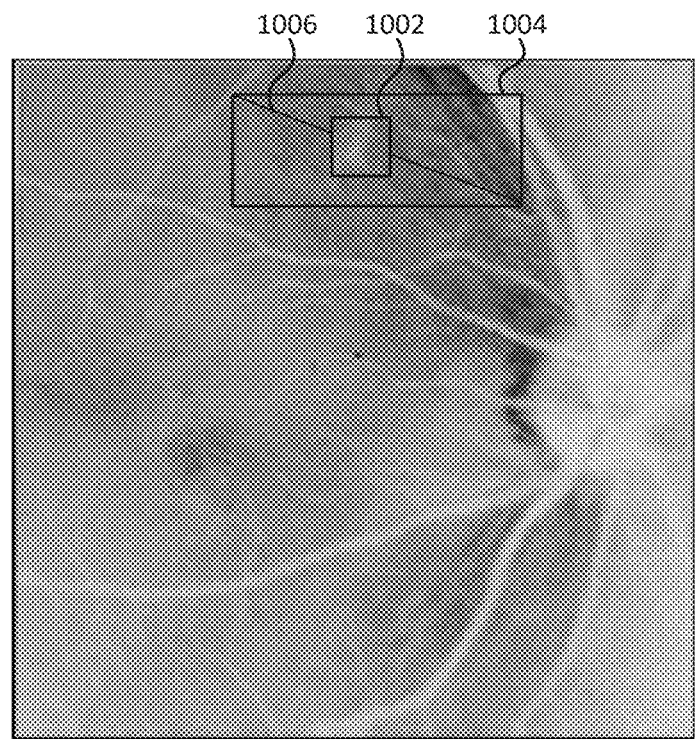
FIG. 10B depicts the image of the eye of FIG. 10A with the floater identified.

FIG. 10A depicts an image of an eye with a floater. The captured image is a single frame image captured from an SLO imaging device. The image 1000 includes at least one floater along with additional features of the eye, such as the retina, veins, etc. FIG. 10B depicts the image of the eye of FIG. 10A with the floater identified. The floater is identified with a bounding box 1002. The location can be used to control the imaging location of the OCT imaging device. For example, depth slices can be captured by the OCT imaging device between the region identified by lines 1004a, 1004b.

Figure 11:
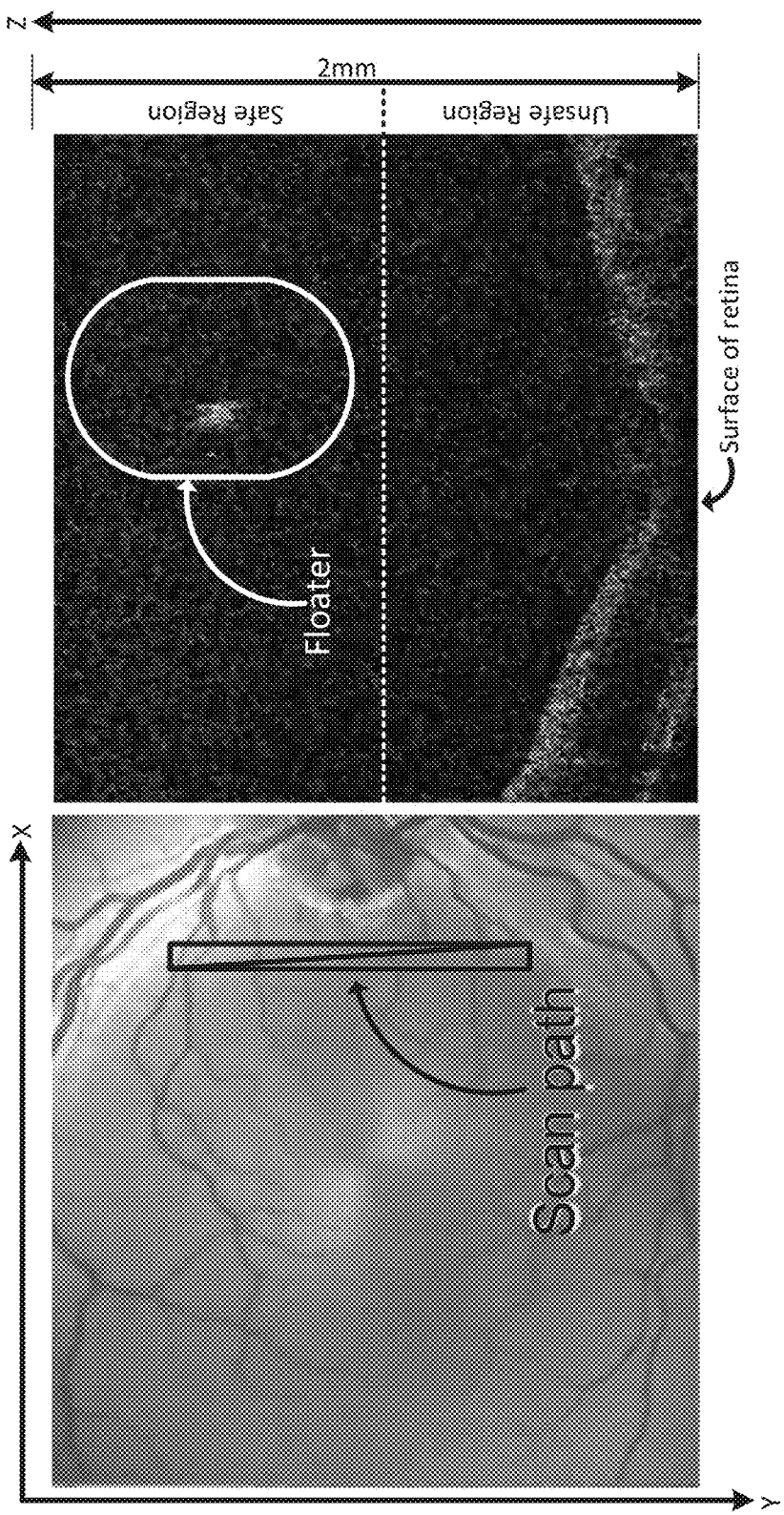
FIG. 11 depicts an SLO image and corresponding OCT image

FIG. 11 depicts an SLO image and corresponding OCT image. The SLO image 1102 provides an X-Y image of the eye or portion of the eye. The floater, or a shadow of the floater can be detected within the image and a scan path for OCT imaging determined that will capture the floater. The scan path is depicted in FIG. 11 as a diagonal line within a bounding box. The scan path determined from the SLO image is used to control the scanning location of the OCT imager. The OCT imager captures depth information along the scan path. The OCT imager can capture a depth image 1102, which may be referred to as a b-scan image, along the scan path. The OCT imager may not be able to capture the entire depth of the eye or vitreous at one time. For example, the depth captured in the OCT image 1302 is 2 mm. The 2 mm depth within the eye that the OCT imager captures can be adjusted by adjusting a focus of the imager. The floater can be detected within the OCT image as depicted in FIG. 11. If no floater is detected in the OCT image, the imaging depth can be adjusted to image the eye at a different depth along the scan path. With the floater detected in both the SLO image 1102 and the OCT image 1104, the 3D location of the floater can be determined. In addition to the floater, the images 1102, 1104 can be used to determine locations of structures or other features of the eye. For example, the veins are clearly evident in the SLO image. Additionally, the surface of the retina can be seen at the bottom of the OCT image. Detected or identified structures within the eye, such as the retina, can be used to set or define safety requirements of treatment lasers, or imaging lasers. For example, it may be undesirable to focus a laser within 1 mm of the retina. Although FIG. 11 depicts the regions as being safe or unsafe based on the proximity to the surface of the retina, it is possible to define more complex safety regions. For example, a laser can be focused within a certain distance of the retina less than 1 mm if it is below a certain power level or duration, however no laser may be focused within a tighter threshold regardless of the power or duration.

The above has described systems and methods for the detection, tracking and possible treatment of SVOs. The real-time tracking of the SVOs allows the SVOs to be targeted by a treatment laser which can reduce the size of the SVOs. The real-time tracking, targeting and treatment of the SVOs can be complicated by the movement of the SVOs. As described further below, various techniques can be employed to control, or at least affect, the motion of SVOs.

Figure 12:
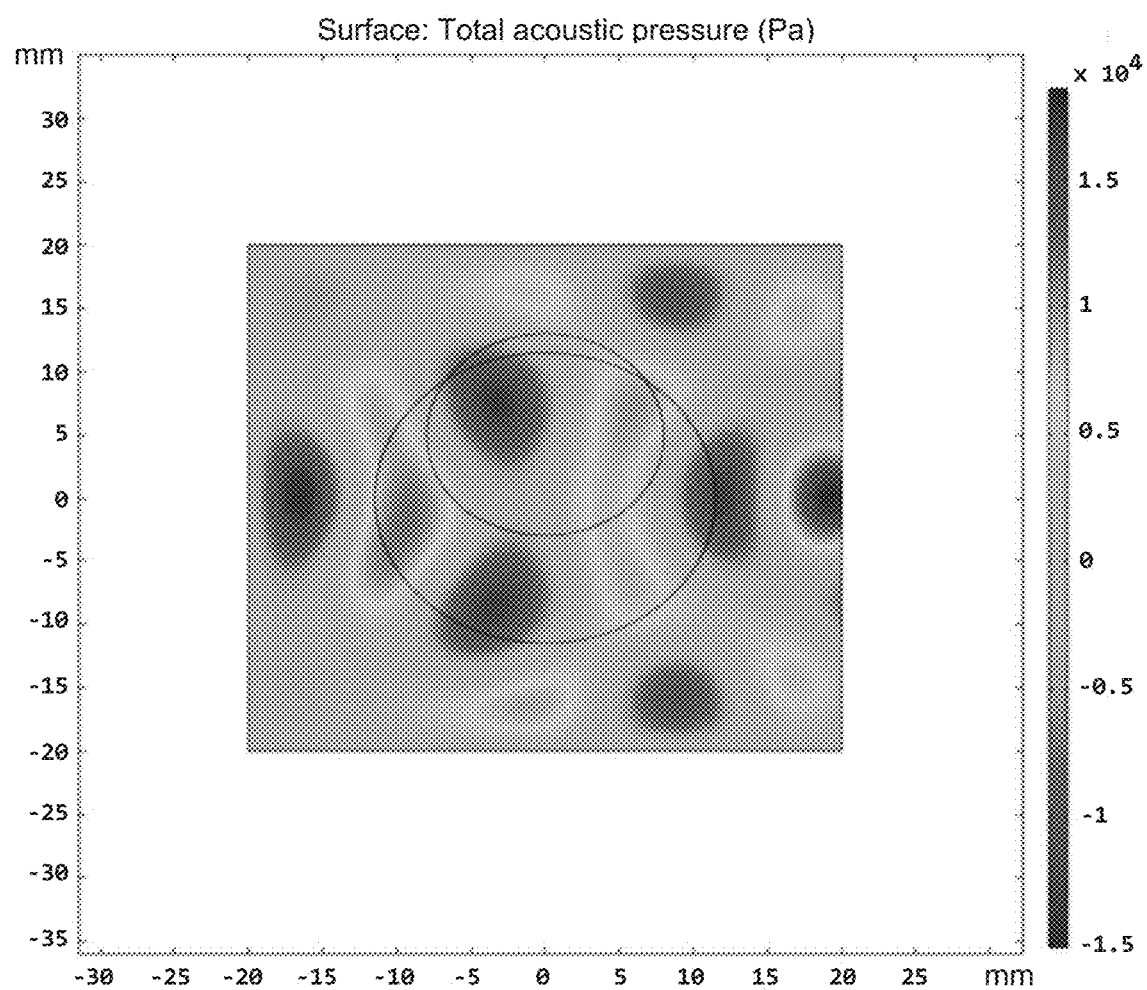
FIG. 12 depicts simulation results of pressure waves within an eye.

FIG. 12 depicts simulation results of pressure waves within an eye. The pressure waves can be transmitted into the eye using bone transducers that can be placed, for example, on the jaw bone. Bone transduction can use relatively low frequency waves that pass into the eye, creating pressure waves within the vitreous humor of the eye. Additionally, or alternatively, the pressure waves within the eye can be provided by a transducer coupled directly or indirectly to the eye. For example an ultrasonic transducer can be coupled to the cornea of the patient's eye. A transducer coupled to the eye can provide higher frequency sound waves into the patient's eye. As depicted in FIG. 12 the pressure waves can provide regions of high pressure 1202 and low pressure 1204 within the patient's eye 1206. The high pressure areas will tend to push the SVOs towards the low pressure areas within the eye. The SVOs can still move within the vitreous humor, however, with the SVOs tending to be moved to the low pressure areas movement of the SVO can be reduced which can improve the ability to treat the SVOs by increasing an amount of time the SVOs stay within a region that can be safely targeted by a treatment laser.

As described above, pressure waves within the vitreous humor can be used to affect movement of SVOs. While the pressure waves can be useful in affecting the SVO movement, additional techniques can be used, possibly in conjunction with the use of pressure waves described above.

Figure 13:
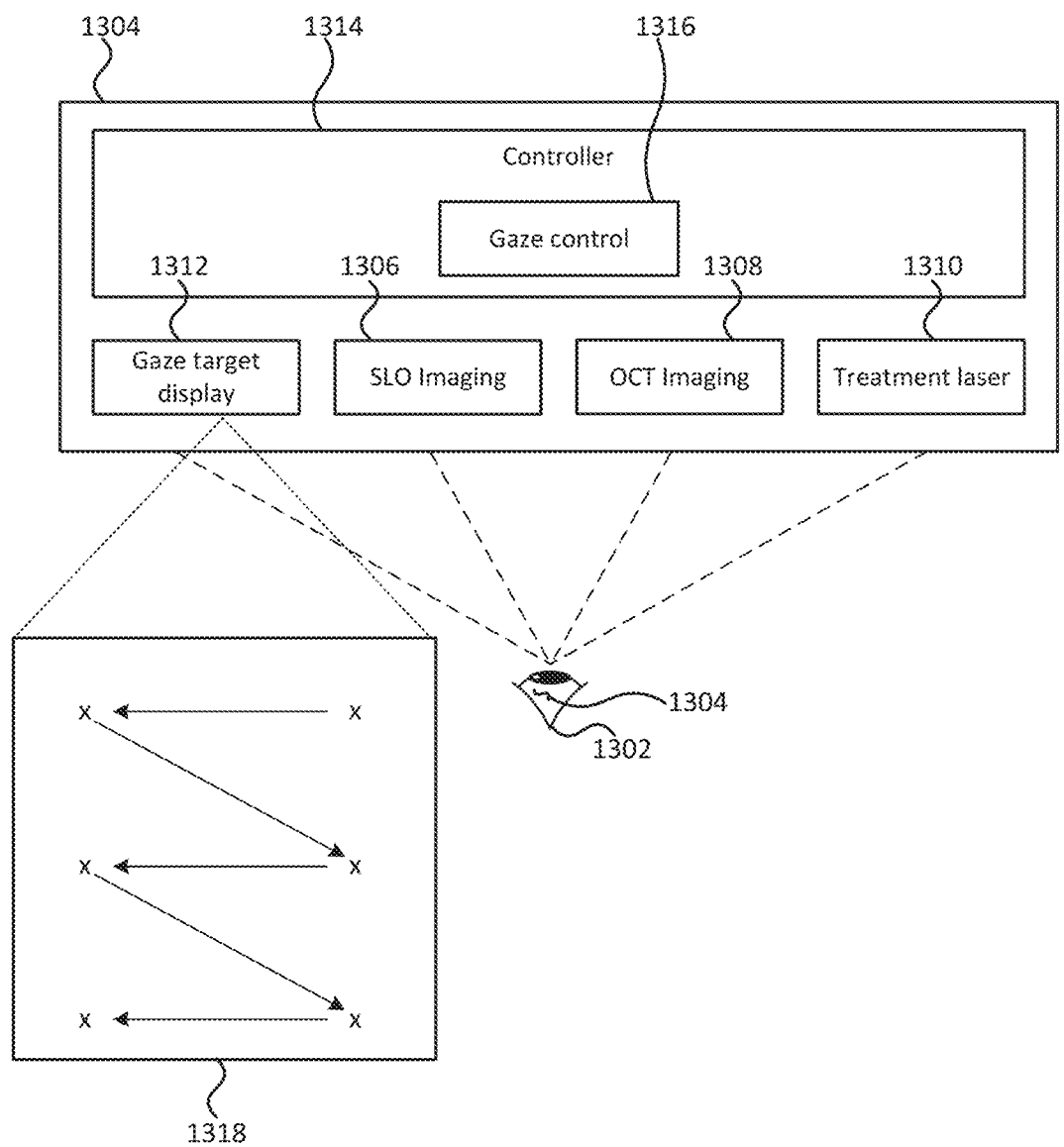
FIG. 13 depicts a use of a laser to affect motion of a floater.

FIG. 13 depicts an optical device with a gaze target display. It is noted that not all possible components of the distributed system are depicted in FIG. 13. For example, the device 1304 may include additional components such as optical imaging components, additional sensors, adaptive optics/lenses or other components. The optical device and gaze target display can be used to control motion of a patient's eye 1302, which in turn can cause motion of the vitreous humor and so the SVOs 1404 within. The device 1304 can be similar to those described above. The device 1304 can include one or more different imaging systems such as an SLO imaging system 1306, and an OCT imaging system 1308 as well as a treatment or therapeutic laser 1310. In addition to the imaging and treatment systems, the device 1304 further includes a gaze target display 1312. The device includes a controller 1314 that is used to control the imaging and treatment systems as well as the gaze display 1312. The controller 1414 provides gaze control functionality 1316 that can control the gaze target display 1312 in order to control movement of the patient's eye. The gaze control can use information from the imaging systems in order to detect and track SVOs. This tracking information can be used to predict a path of the SVOs and determine eye motion that can counter the movement of the SVO.

The gaze control functionality 1316 generates targets that, assuming the patient looks at the targets, move in order to cause the patient's eye to move in a manner that at least partially counteracts the SVO movement. The target positions and movement are programmed to move in such a way as to induce a specific movement in the patient's eye. This is used to achieve a desired eye movement, which is calculated to cause a predictable and desirable motion in the floaters of interest. The generated targets can then be displayed on the gaze target display 1312 as depicted by illustrative target display 1318. The target display 1318 is depicted as providing a moving target, 'X', that the patient follows. It will be appreciated that although multiple targets are depicted in the display 1318, it is intended to depict a single target that moves over time in a determined manner.

The display 1318 provides a screen that's displayed to the patient while the eye is being imaged and can be used for various purposes. The display can be used to identify specific floaters that are symptomatic or bothersome to the patient. The display can display a white screen or grid that can make the floaters more visible to the patient. The doctor can select a floater being tracked by the system using a user interface. The floater can be highlighted in the patient's vision, possible using the OCT light or by changing a portion of the screen to highlight the floater. Using this technique, the patient can guide the doctor quickly to select the correct floater. This can be used both for diagnostics and treatment of floaters. Other techniques can be used to identify particular floaters that are symptomatic or bothersome to the patient including using the display to present the user with text to read. The speed of reading, or the ability to read can be used as an indication of the severity of an SVO being tracked that is in the patient's view of the text being read.

Figure 14:
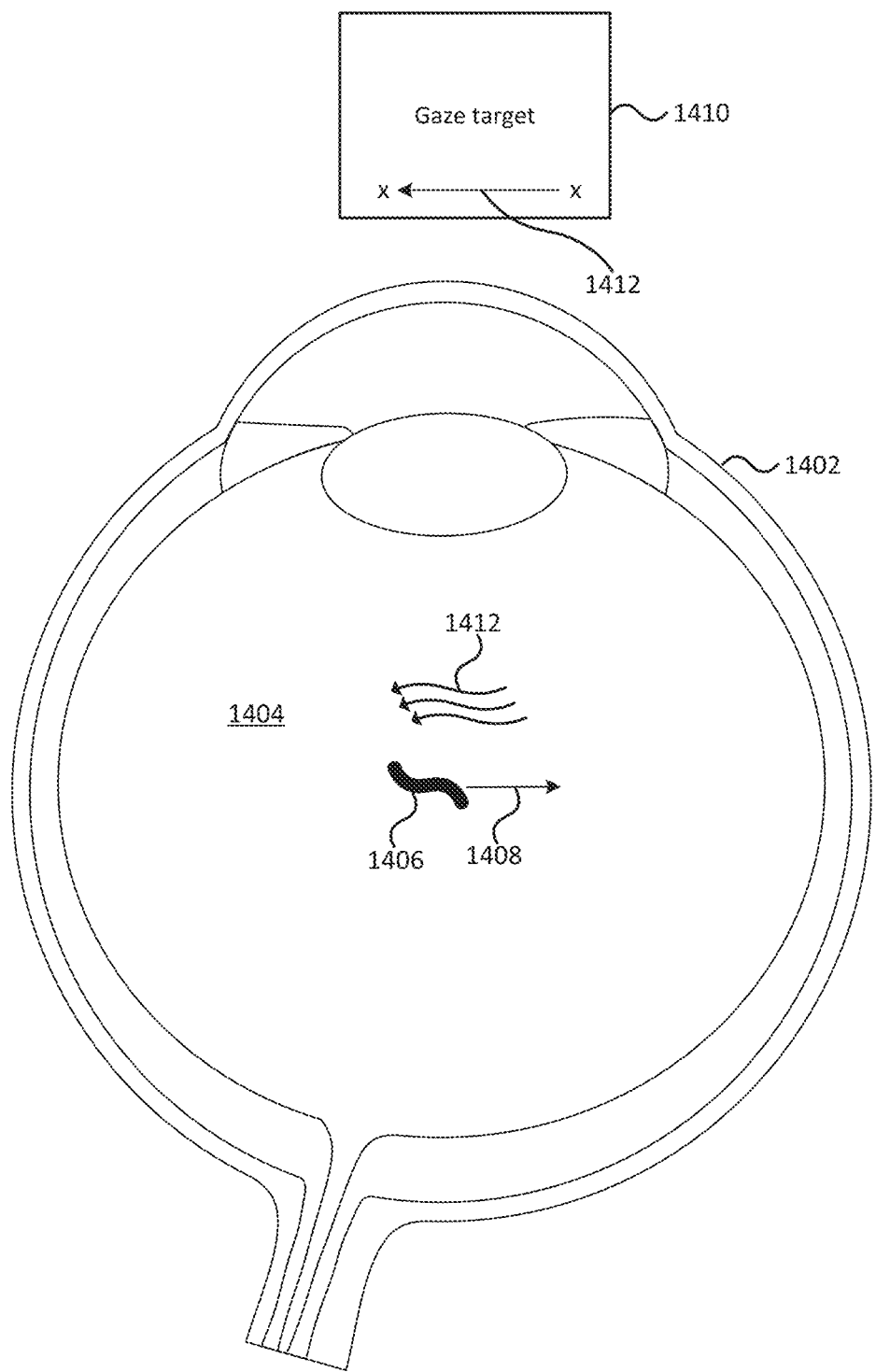
FIG. 14 depicts an optical device with a gaze target display.

FIG. 14 depicts a use of a gaze target to affect motion of a floater. An eye 1402 is depicted with vitreous humor 1404 that has an SVO 1406. The SVO 1406 moves within the vitreous humor as depicted by arrow 1408. Although not depicted in FIG. 14, the position of the SVO can be tracked using one or more imaging systems as described above. The tracked SVO can also be targeted by a treatment laser in order to break up the SVO or otherwise reduce its size.

A gaze target 1410 is displayed to the user with a target 1412 being moved in the gaze target display as depicted by arrow 1414. The target 1412 is moved in a manner that attempts to counteract the motion of the SVO. As the patient follows the gaze target 1412, the vitreous humor will be caused to move in a similar direction depicted by arrows 1416. The movement of the vitreous humor, induced by movement of the patient's eye following the gaze target, can at least partially counteract movement of the SVO 1406.

Figure 15:
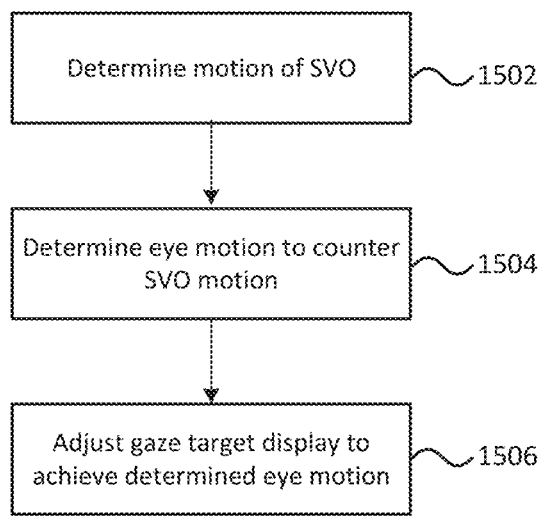
FIG. 15 depicts a use of a gaze target to affect motion of a floater.

FIG. 15 depicts a method of using a gaze target to affect motion of a floater. The method 1500 can be performed by various components of a device. It will be appreciated that the method can be performed partially on the optical device and partially by other computing devices in communication with the optical device.

The method 1500 determines motion of an SVO (1502). Determining the motion of the SVO can be done by, for example by detecting and tracking an SVO and determining its motion and possibly the predicted future motion, based on the tracking. The detection and tracking and subsequent future motion prediction can be performed by separate components, using possibly classical computing approaches and/or machine learning models trained to perform the particular task. Additionally, or alternatively, one or more of the detecting, tracking and future motion prediction can be combined together into a single component. For example, a single machine learning model can be trained to identify an SVO predict future motion of the SVO based on a series of images of one or more modalities. With the motion of the SVO determined, an eye motion of the eye that can at least partially counter the SVO motion is determined (1504). The determination of the counteracting motion can be done in various ways. For example, known motion of the eye can be correlated with motion of the vitreous humor, which in turn can be used to estimate an effect on the SVO motion. Additionally or alternatively, eye movement and the effect on SVO motion can be measured across a range of patients and SVOs in order to generate an eye movement model that can counteract SVO movement. Once the eye movement is determined to at least partially counteract the SVO motion, a gaze target is displayed to the user in order to achieve the desired eye motion.

The gaze target display can be operated in order to have the patient move their eye in a predetermined pattern and the effect of the motion on one or more SVOs can be monitored. The information can be used in order to determine possible eye motion to counteract SVO motion. Further, rather than countering the motion of SVOs that gaze display can be used to cause the patient to move their head/eye in a pattern that helps bring the right floater to the imaging and treatment field of view. Further, sequence of gaze procedures can be provided to allow all, or substantially all, of the floaters to be detected. Further using particular sequence and speed of gaze and amplitude of gaze change, it is possible to extract additional measurements/characteristics of the SVOs such as position of the floater in the vitreous (i.e. distance from the retina), speed of motion, opacity, density, etc.

The gaze target display can also be used for other purposes beyond affecting movement of SVOs. For example, the gaze target display can present text for a patient to read. As the patient's vision is affected by SVOs, which can be simultaneously tracked, the ability to read the displayed text can be correlated to the SVO being tracked that is obscuring the patient's vision. That is, the gaze display can be used to collect, and correlate to particular SVOs, subjective information from the patient about the severity of SVOs. That is, the gaze display can be used to provide a correlation between what the patient sees and what the doctor sees. This can be helpful in identifying floaters exactly are the bothersome floaters for the patient, which is currently a challenge.

The subjective information collected from the patient about the severity of SVOs, or the impact SVOs have on their vision, can be combined with the different imaging modalities of the SVOs in order to train an SVO classifier that classifies images, possibly of both modalities namely SLO and OCT, of the SVOs based on a severity of the SVO.

Figure 16:
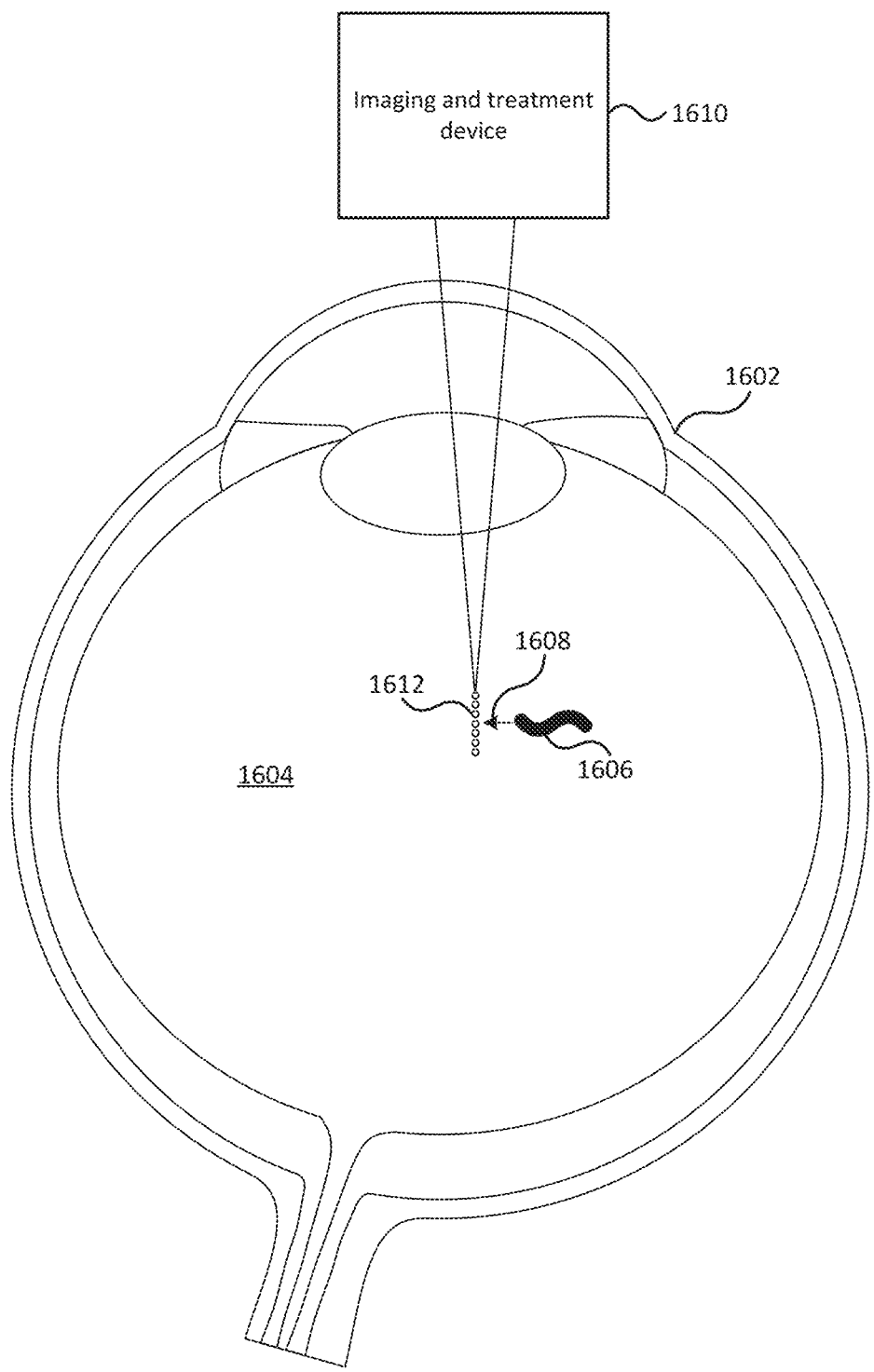
FIG. 16 depicts a method of using a gaze target to affect motion of a floater.

FIG. 16 depicts a use of a laser to affect motion of a floater. As described above, the imaging and treatment device can include a treatment laser which can be, for example a femtosecond laser can be used as the treatment laser. In addition to using the treatment laser to target the SVOs, and possibly break them up or reduce them in size, the treatment laser can also be used to control or at least affect motion of the SVO.

An eye 1602 is depicted with vitreous humor 1604 that has an SVO 1606. The SVO 1606 moves within the vitreous humor as depicted by arrow 1608. Although not depicted in FIG. 16, the position of the SVO can be tracked using one or more imaging systems as described above. The tracked SVO can also be targeted by a treatment laser in order to break up the SVO or otherwise reduce its size. The movement of the SVO can be affected using the treatment laser by targeting the vitreous along the path of motion of the SVO. The treatment laser can vaporize the vitreous where targeted creating small bubbles 1612 that can act as a barrier slowing the motion of the SVO. The particular location to target can be based upon and predicted motion of the SVO.

Various techniques have been described above that can each affect, at least to some degree, movement of an SVO. Although described individually, it will be appreciated that one or more of the techniques can be used in coordination with each other. Further, although described with respect to a single SVO, it will be appreciated that each of the techniques, whether used individually or together, can be used on multiple SVOs.

As described above, one or more SVOs can be detected, tracked and possibly characterized using one or more imaging modalities. The SVOs can be targeted by a treatment laser. The exact pattern used for targeting the SVO with the laser can vary. For example, a 3D surface of the SVO can be generated based at least in part on the imaging data, and the surface of the SVO targeted by the laser. While such an approach is possible for treating SVOs, it can be difficult to generate the target pattern required to treat the SVO. An additional approach to defining the laser scanning patterns, parameters, and techniques for efficient and effective treatment of SVOs is described with regard to FIGS. 17A and 17B.

Figure 17A:
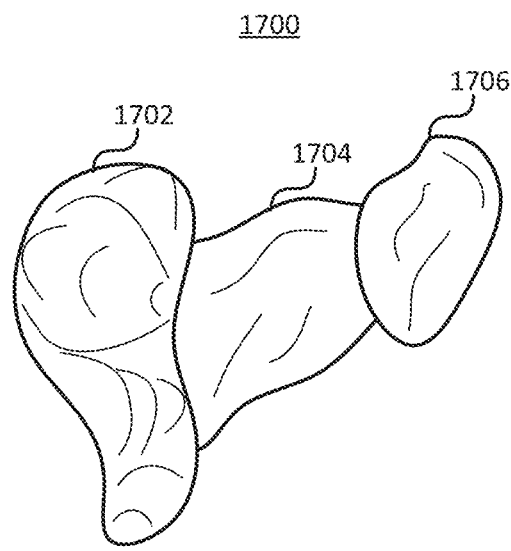
FIG. 17A depicts an illustrative SVO.
Figure 17B:
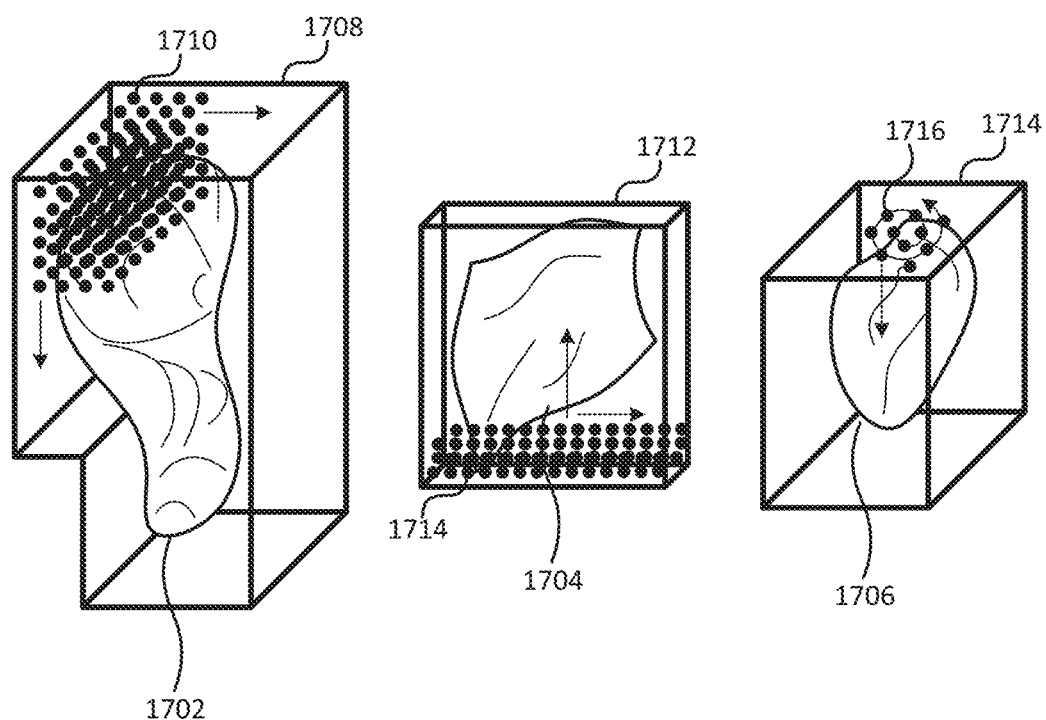
FIG. 17B depicts target volume enclosing the SVO of FIG. 17A

FIG. 17A depicts an illustrative SVO. It will be appreciated that individual SVOs may have a wide range of shapes and sizes. The SVO 1700 depicted in FIG. 17A has a large blob or structure 1702 that is connected to by a sheet-like structure 1704 to a smaller blob or structure 1706. T FIG. 17B depicts geometric target volumes for the SVO 1700. As depicted in FIG. 17B, an SVO 1700 may be segmented into a plurality of different portions or regions and a geometrical 'target volume' can be defined based on 3D imaging of the SVO that encompasses one or more of the different regions. The individual target volumes may be arranged such that taken together, all of the SVO 1700, or the most critical volume(s) for treatment of the SVO are within a target volume. Three separate target volumes are depicted as enclosing the SVO. A first target volume 1708 encloses the SVO blob portion 1702, second target volume 1712 encloses the sheet-like connective structure 1704 and a third target volume 1714 encloses the second blob structure 1706. The SVO 1700 can be a single SVO or a group of SVOs that are located inside a well-defined three dimensional space.

The target volumes 1708, 1712, 1714 enclosing portions of the SVO can be used in creating a laser scan pattern, depicted as dots 1710, 1714, 1716. It will be appreciated that the scan pattern can substantially fill the entire geometric target volume. In addition to the scan pattern the SVO treatment can also define one or more laser parameters such as pulse duration, number of pulse, power, etc. The target volume can also be defined as a containment zone where laser scan patterns and the resulting bubbles within the vitreous can provide bounds on floater movement during treatment, also serving to stop or direct SVO motion for better treatment safety and efficacy as described above. Different target volumes may use different scan patterns, which may be determined based on characteristics of the SVO portion, including its structure, shape, size, movement and location. As depicted, scan patterns can progress in various ways such as from the top down as depicted with scan pattern 1710, from the bottom up as depicted with scan pattern 1714 or in other patterns such as a spiral or circular pattern as depicted in scan pattern 1716. Although the scan patterns are depicted as filling the target volume, it is possible for the scan pattern to only target surfaces of the SVO.

The SVOs can be characterized using an aggregate volume of voxels of 3D image data corresponding to specific locations and optical characteristics. A voxel is a volume unit of a 3D image. The 3D image data can be constructed by fusing images of different imaging modalities together. For example, the 3D image data can be provided by fusing SLO images and OCT images of the SVO. Voxels in different zones of the SVO can require different laser and scan parameters. A laser scan pattern defined to fill the geometric target volume with laser pulses of optimized energy and distribution, just above the threshold for photodisruption in a specific voxel for example, can ionize the aggregate target volume containing SVO(s) by efficiently photoionizing them into small gas bubbles, water, and microscopic fragments below the symptomatic threshold for the patient.

By generating a target volume for an SVO, or group of SVOs, allows geometrically well-defined scan volumes for laser treatments to be used rather than complex and variable characteristics of the specific SVO being targeted. The use of such scan patterns can simplify treatment and improve outcomes.

The scan pattern for treating the SVO can be determined in coordination with the scan pattern used in imaging the SVO. The scan pattern of the floater can be a simple geometric grid that fills a volume or can be more complex. For example, the scan can use circular scan patterns, spiral scan patterns, linear scan patterns, or a combination of these patterns. During treatment one possible treatment methodology is to use a scan and treat approach, where first the SVO is scanned using a circular path to image the floater with the OCT and determine where the surface of the floater is located in the Z axis. After the circular scan to determine the surface, the same circular scan can be repeated again but using the treatment laser instead of the OCT and so fire the femto laser at the surface of the floater. The imaging and treatment of the SVO using a circular scan path from the outside to in can help in containing the floater. The focus of the treatment laser can be adjusted based on SVO surface determined from the previous scan. Such and imaging and treatment process can be beneficial as it allows the rapid imaging and subsequent treatment of the SVO in a short enough period of time as to prevent or substantially limit the movement of the SVO between the imaging and treatment.

This allows an SVO to imaged and treated rapidly, without giving the floater enough time to move in between imaging and treating. It can be possible to switch between scan patterns. For example, for a circular scan pattern, as the scan approaches the center it is necessary to scan at increasing speed. The scan modes or patterns can be selected based on various factors.

These laser scan patterns and photoionization bubbles can also be used for restricting floater motion, keeping them in the preferred zone for treatment, dividing them into smaller treatable fragments, and aggregating smaller floaters into larger target volumes. Laser bubble patterns can be used to benefit the imaging and tracking systems by providing reference targets and boundaries, and ensuring target SVOs stay in a preferred treatment zone. Smaller floaters can be 'surrounded' by a ring of bubbles for reference and treatment sequencing. Further, gravity can influence the motion of an SVO and the photoionization bubbles can be generated below the SVO in order to counter or reduce the movement due to gravity.

A treatment centroid, peripheral features, or other characteristics of the SVO target volume can be used for tracking during treatment. Laser pulse energy and treatment parameters on target can be varied to match the characteristics of all the local voxels within the geometric target volume containing the SVOs, thus optimizing the treatment planning and execution. Creating a well-defined geometric shape, or group of shapes, encapsulating the optimum volume in the vitreous containing the target SVO(s) allows a well-defined laser scan pattern to be implemented throughout the target volume, eliminating all SVOs inside the geometric target volume without having to employ complex scan patterns based on the individual SVO surfaces. This scan pattern for treatment can also be optimized for time. Pulses that are focused in the target volume that contain only clear vitreous produce only a small bubble and cause no harm, while pulses that hit the SVO eliminate the material comprising the floater. Other pulses and patterns can be used for containment of floater motion, segmenting SVOs into smaller treatable or sub-symptomatic sizes, or other reasons.

Typically femtosecond scanning laser patterns are executed from posterior to anterior to avoid plasma shielding during treatment which can cause incomplete or interrupted photoionization. A well-defined geometric target volume that accounts for the 3D SVO classification parameters, controlled motion and segmentation of the floaters, and the most effective volume laser scanning methods can produce the most effective treatments In this way, classifying SVOs based on groupings of voxels that define localized energy and parameter requirements for laser photoionization that aggregate into larger well defined target volumes allows fast and efficient laser scanning of the entire vitreous region containing SVOs. Similarly certain peripheral voxels and selected voxel groupings could be used for floater containment and controlled treatment methods. This makes defining, tracking, and treating SVOs more controlled and effective.

The above has described the possible laser treatment of floaters by tracking the floaters and subsequently targeting the floaters with a laser. The tracking and targeting process described above can be combined with other techniques to possibly contain or affect movement of the floaters. Additionally, other techniques can be combined with those above either to improve the efficacy of the treatment and/or the safety of the treatment For example, one treatment technique attempts to coat gold nanoparticles (AuNPs) with anionic hyalouronan (HA). HA has an affinity to vitreous collagen which can form floaters. The HA-AuNPs are attracted to the floaters and subsequent illumination of the HA-AuNPs with laser pulses of an appropriate wavelength causes a rapid temperature increase on the AuNP surface. The rapid temperature causes evaporation of the surrounding water which forms vapour nanobubbles. The vapour nanobubbles quickly expand and collapse, in tens to hundreds of nanoseconds, which can ablate the collagen of the floaters. While this use of nanoparticles still requires laser treatment of the eye, the laser power required to cause formation of the vapour nanobubbles can be lower than required to directly ablate the floaters. Accordingly, the treatment can be safer as a lower power laser can be used.

The tracking and targeting of floaters as described above can be combined with the nanoparticle mediated ablation. That is, the floaters can be tracked and targeted using a laser after injection of HA coated AuNPs. The HA-AuNPs are attracted to the floaters, which can be tracked and targeted by the laser as described above. By combining the two techniques greater safety, and or improved floater ablation, can be possible with lower power laser pulses. Further, rather than using HA to coat nanobubble forming nanoparticles it can be possible to use other compounds such as indocyanine green (ICG) which have an affinity to collagen. The particles can have a certain dimension that allows them to be injected into the patient's eye and be selectively attracted to the floaters or other structures being targeted. In addition to the affinity for the structures being targeted, the particles also have a plasmonic resonance at the wavelength, or wavelengths of the treatment laser. The particles lower the power required to cause ablation.

Further, the above has described the use of nanobubble forming nanoparticles coated with a particles having an affinity to the collagen of floaters in order to safely target and treat the floaters using the floater targeting and treatment described above, it can be possible to use a similar process to track and target other structures of the eye or within the vitreous.

Figure 18:
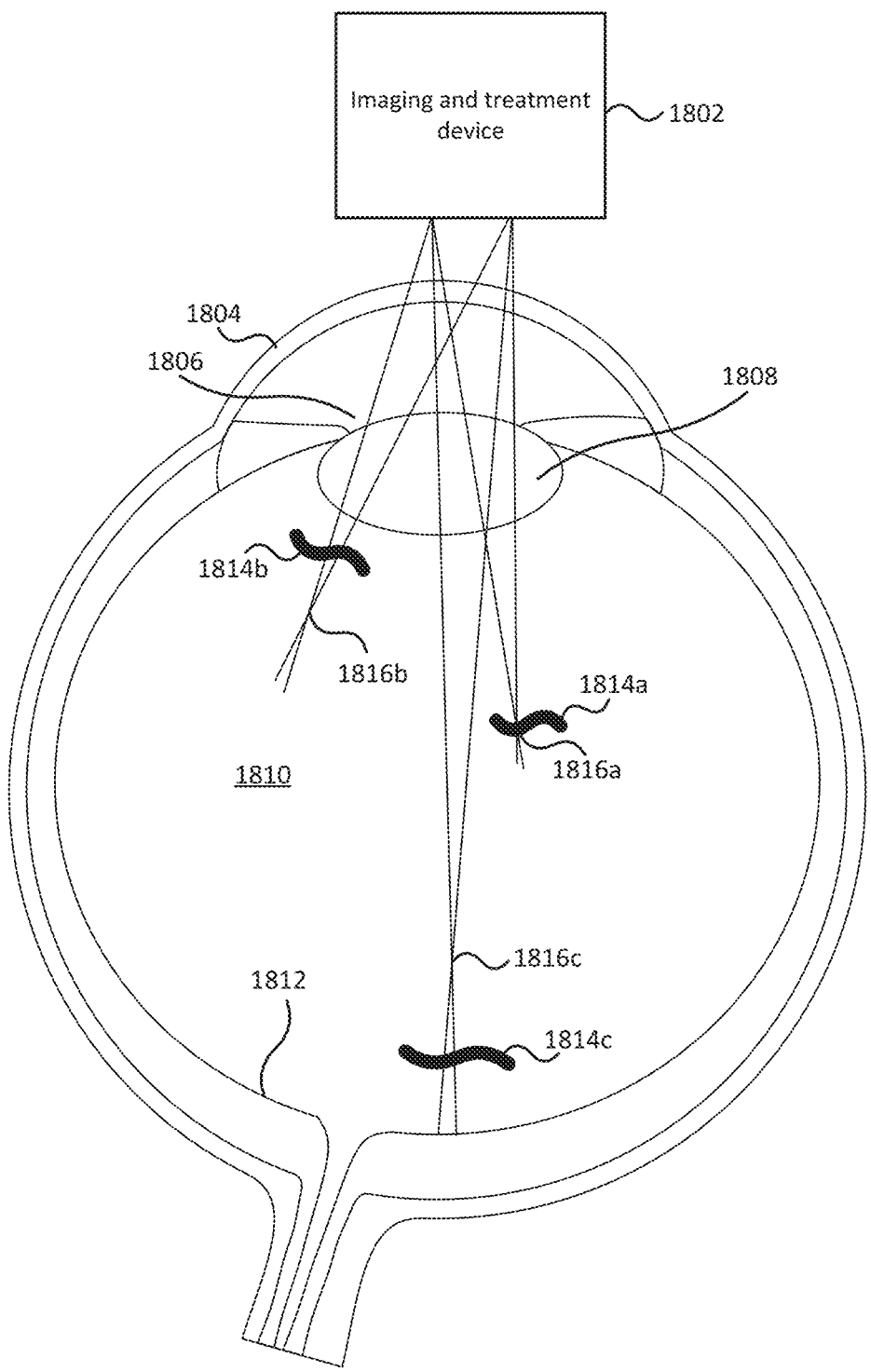
FIG. 18 depicts a process for nanoparticle-mediated laser treatment of floaters.

FIG. 18 depicts a process for nanoparticle-mediated laser treatment of floaters. The floater treatment process can be carried out by an imaging and treatment device 1802 such as described above. The process assumes that the patient's eye 1804 has been injected with nanoparticles as described above. The patient's eye can include one or more areas that are unsafe for laser treatment. For example, these areas can include a retina of the eye 1806 and a lens of the eye 1808. These unsafe areas can be damaged by the laser, and negatively affect the patient's eye sight. As described further below, the tracking and treatment functionality can be combined with the nanoparticle-mediated treatment in order to safely treat floaters even in close proximity to the unsafe treatment locations within the eye such as the retina 1806 and/or lens 1808.

As depicted in FIG. 18, a number of floaters 1810a, 1810b, 1810c (referred to collectively as floaters 1810) can be located within the patient's eye. The floaters 1810 can be imaged and tracked by the tracking and treatment device 1802 as they move within the patient's eye. Three different floaters 1810a, 1810b, 1810c are depicted with a first floater 1810a generally being located in a safe treatment area, which can be considered as an area in which focused laser light will not damage important tissues or structures. When treating the floater 1810a in the safe location, the treatment laser of the tracking and treatment device 1802 can be safely focused, as depicted by focus point 1812a onto the floater 1810a in order to cause ablation. The focused laser light can have sufficient power to cause ablation of the floater. Since the floater 1810a is in a safe location, a higher power laser can be used to increase the ablation without risk of damaging other tissue. The focused laser can be scanned across the floater or a geometric volume containing the floater in order to cause a complete, or near complete ablation of the floater 1810a.

A second floater 1810b is depicted as being in an unsafe location, namely in close proximity to the lens 1808. The risk of incorrectly targeting the floater and accidentally focusing the high power laser on the patient's lens, and so damaging the lens can be unacceptably high. With the nanoparticles bonded to the floaters 1810 ablation can still occur at power levels below the fully-focused power level of the laser. These lower power levels can be considered safe to be used even in the unsafe areas of the retina 1806 and/or lens 1808. While the power of the laser could be reduced in order to have the lower power level when fully focused, it can be possible to focus the higher power laser past the floater 1810b as depicted by focus point 1812b, so that the focus point is located posteriorly to the floater. As depicted in FIG. 18 by focusing the high power laser at a posterior location of the floater 1810b, the de-focused laser light falling on the floater 1810b is at a lower power so as to be safe for use in such close proximity to the lens 1808. Although the laser light is not focused, the laser light on the floater is still of sufficient power to cause the nanoparticle-mediated ablation of the floater 1810b. Further, the unfocused light, while still delivering a desired power level can provide the power over a larger area.

The floater 1810c, similar to the floater 1810b, is located in an unsafe location, namely in close proximity to the retina 1806. In this case, the laser can be focused before the floater, that is on an anterior side of the floater. The laser is focused before/anteriorly to the floater 1810c as depicted by focusing spot 1812c to ensure that the power of the laser light on the retina is within safe levels. While the de-focused laser light on the retina may not be of sufficient power to cause damage to the retina, it is still powerful enough to cause the nanoparticle-mediated ablation of the floater 1812c.

When focusing on an anterior or posterior side of the floaters 1810b, 1810c, the floater can wholly fall within the area of the defocused laser light and as such the entire floater can be ablated at once. Alternatively, only a portion of the floaters 1810b, 1810c can fall within area of the defocused laser light and the laser can be steered across the floater in order to treat the different portions of the floaters. Alternatively, the unfocused laser can be targeted at a plurality of different locations defined in a scan pattern, which can be defined as described above or using alternative techniques.

The above has described a imaging and treatment systems and devices that can use lasers in the treatment, and possibly imaging. While the above has described various ways to improve the safety of such laser treatment, including determining if the treatment can be in a potentially unsafe area of the eye, as well as nanoparticle-mediated treatment to reduce potential power levels of the treatment laser. While each of these techniques can provide sufficient safety, given the importance of a patient's eye, additional safety measures can be provided. It will be appreciated that the safety measures can be used individually or in combination.

Figure 19:
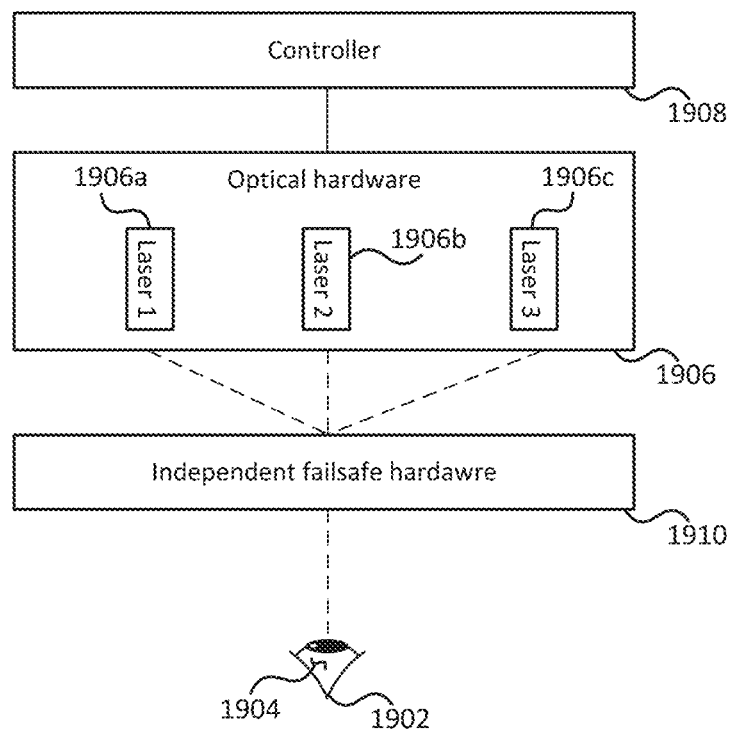
FIG. 19 depicts an optical system including independent failsafe hardware.

FIG. 19 depicts an optical system including independent failsafe hardware. The system is depicted as an imaging and treatment system for an eye 1902 with one or more floaters 1904. Although described with reference to floater treatment, it will be appreciated that it can be used in other imaging and/or treatment systems that use lasers. The system includes various optical hardware 1906 including one or more lasers 1906*a*, 1906*b*, 1906*c* that can be used for imaging and/or treatment purposes. The optical hardware 1906 can be controlled by controller 1908, which can be provided by one or more processors, controllers, microcontrollers etc. The controller controls the optical hardware in order to provide the desired imaging and treatment functionality. The system can further include independent failsafe hardware 1910 that provides a failsafe mechanism to ensure the lasers of the optical hardware do not cause damage to the patient's eye.

The independent failsafe hardware works independently from the controller 1908 and can monitor signals, including but not limited to SLO laser power, SLO scanners, OCT laser power, OCT scanner, surgery laser power, surgery laser firing duration, number of the pulses, surgery laser treatment location, eye movement and other parameters that can be useful in determining safety of the use of one or more of the lasers. The independent failsafe hardware can independently determine to stop any laser in the system from firing with control lines if any hazards present to the patient. Hazards detected by the system include but are not limited to stationary SLO laser firing in the eye, high SLO laser power, stationary OCT laser firing in the eye, high OCT laser power, wrong location treatment, wrong floater targeted, excessive surgery laser power, and extended surgery laser fire duration. The independent safety hardware can be provided by for example an ASIC, FPGA, analog electronics, watchdogs, DSPs and redundant processing units.

Figure 20:
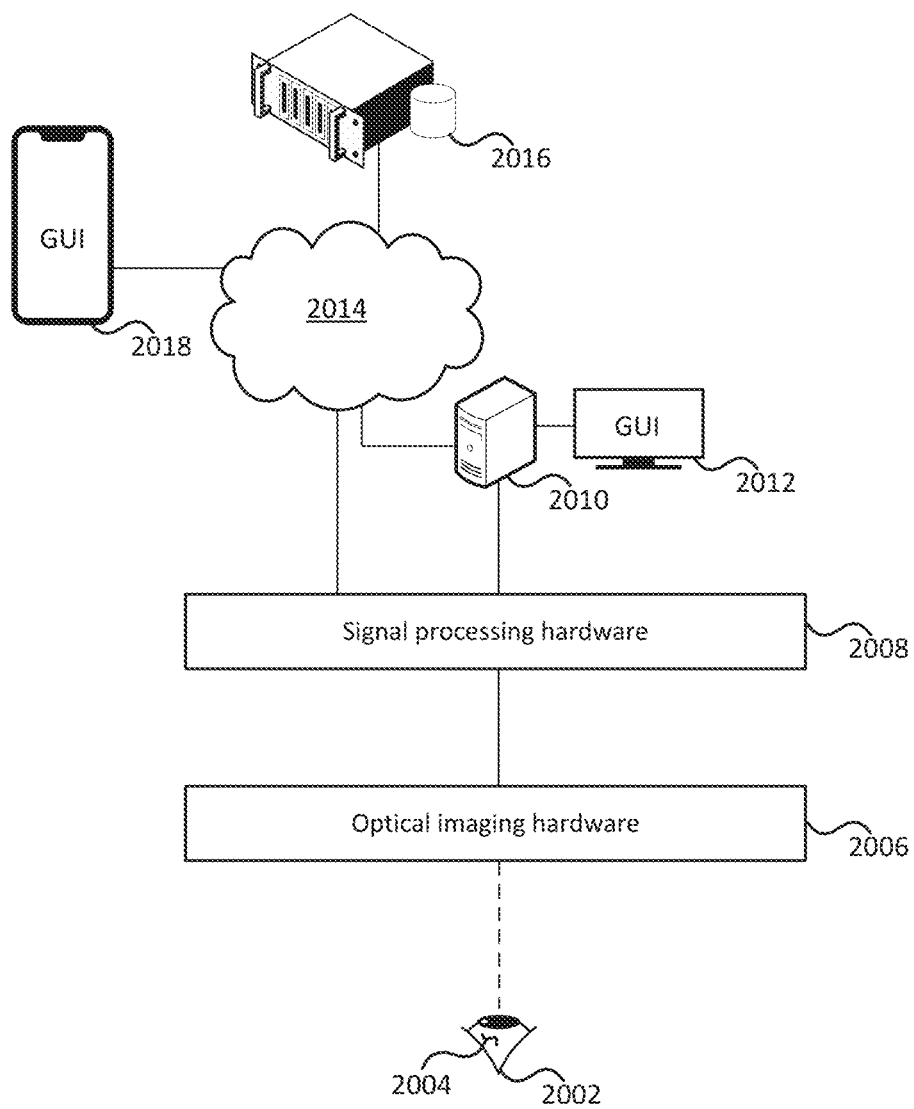
FIG. 20 depicts an optical imaging system.

FIG. 20 depicts an optical imaging system. The optical system 2000 can be used in order to image a patient's eye 2002 that can have one or more floaters 2004. Although described as providing only imaging functionality, it is possible that such a device could also incorporate treatment functionality. The device can comprise optical imaging hardware 2006 that can capture images of the patient's eye. The device can be a low cost device providing only a single imaging modality such as a fundus imaging device or SLO device, or can provide multiple imaging modalities such as fundus imaging, SLO imaging and/or OCT imaging systems. The optical imaging hardware 2006 is controlled by processing hardware 2008 that can either comprise processing functionality for processing the image data directly on the device. Depending upon the processing capabilities of the processing hardware, the device can implement various imaging and detection functionality as described above. The processing hardware can be provided by an FPGA, ASIC, or can be provided by a processor/microprocessor. The processing can identify the presence, and possibly a severity of floaters in a patient's eye as well as whether or not the floaters would be good candidates for laser treatment. Additionally or alternatively, the on-device signal processing can be relatively basic and can pass the captured image data to another computing device further processing. The additional computing device can be a local computer 2010 or computing device that can process the captured images to identify ocular conditions as well as present a graphical user interface (GUI) 2012 to a user. Additionally or alternatively, the processing hardware of the device 2008 can communicate with one or more processing devices over the internet or other network 2014. The remote processing devices can include a remote processing computer for processing the image data as well as possibly generating a GUI for presentation to the user 2016. The computing device can also include a computing device such as a phone or tablet that can process the images data or simply display a GUI. It will be appreciated that the device with the optical imaging hardware and signal processing hardware can be used to provide a low cost, distributed system that can image a patient's eye and provide an indication of the presence of floaters that could be treated by a laser.

As described above, the optical imaging hardware 2006 can comprise a single imaging modality such as a fundus camera or SLO imager. The image processing, whether performed by the signal processing hardware 2008 or one of the remote computing devices 2010, 2016, 2018, can use a machine learning model in order to identify floaters within the captured images.

Figure 21:
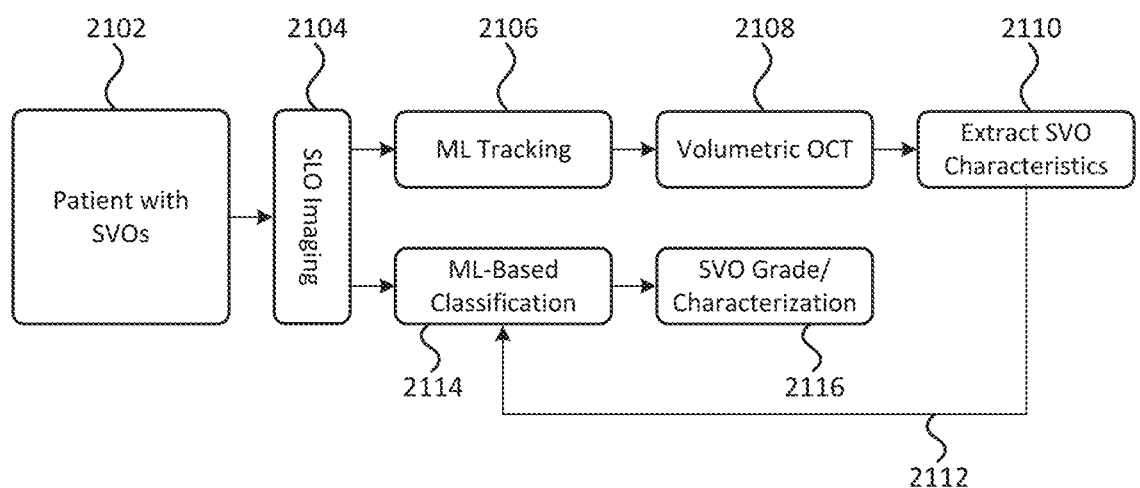
FIG. 21 depicts a process for training a machine learning model for classifying floater.

FIG. 21 depicts a process for training a machine learning model for classifying floaters . . . . The model can be trained using 2D and 3D data in order to classify SVO s using only 2D data. The model can simulate a 3D volume of the floater based on 2D information. The characteristics of the SVOs can also be generated by the model from the 2D information. The training of the model can be supervised, semi-supervised or unsupervised. In order to train a machine learning (ML) model, a patient with SVOs 2102 is subjected to SLO imaging 2104, or possibly other fundus imaging. The captured images are used to identify and track in real-time one or more SVOs 2106. Volumetric OCT 2108 is performed in order to extract SVO characteristics 2110 such as depths of the SVOs within the eye, a count of the number of SVOs, sizes of the SVOs, opacities of the SVOs, etc. The SVO characteristics extracted from the volumetric OCT data are then used as feedback for training an ML-based classification model 2114. The ML classification model is trained using the feedback extracted from the volumetric OCT to classify SVOs 2116 based only on the SLO imaging, or fundus image. The training data obtained from the volumetric OCT contains more detailed information than data from the SLO. Once trained, the ML classification model can be deployed to one or more imaging devices in order to classify floaters based only on the SLO or fundus images.

Figure 22:
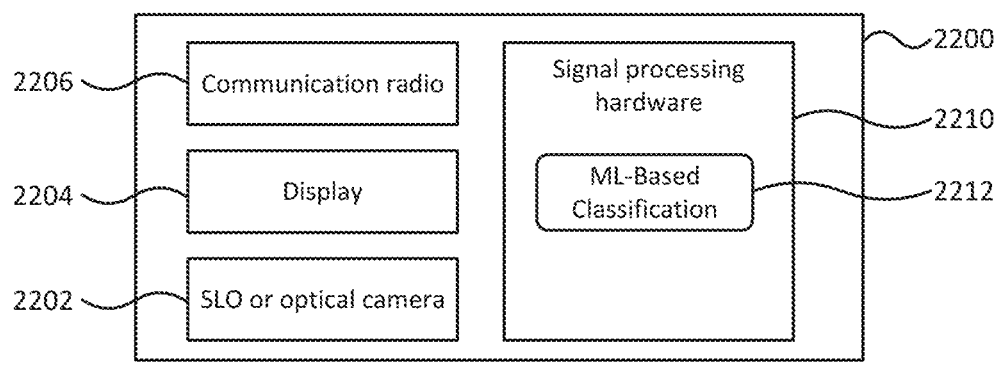
FIG. 22 depicts an optical system using a trained machine learning model for classifying floaters.

FIG. 22 depicts an optical device using a trained machine learning model for imaging, quantifying, screening and classifying floaters. The device 2200 can provide a low cost device that captures images and processes them using the trained ML classification model to classify SVOs within the patient's eye. The classification can provide an indication to the patient as to whether or not they would be a possible candidate for further treatment of the SVOs. The device 2200 can comprise an SLO imaging system or an optical camera 2202 along with the optical pathways and elements such as lenses necessary to image the patient's eye. The device can comprise a display 2204 that can communicate the classification information to the patient. The display can be as simple as a light or led indicating that they are or are not a good candidate for treatment or can comprise more complex display options such as a display capable of displaying text and or graphical information to the user. The device 2200 can further include a communication radio or modem 2206 which can be either a wired or wireless radio or modem allowing the device 2200 to communicate with remote computing devices. The device 2200 includes signal processing hardware 2210 that processes the images captured by the SLO or optical camera 2202. The signal processing hardware 2210 can implement a trained ML classification model 2212 such as that described above.

It will be appreciated that the device 2200 can be provided as a low cost device, or possibly incorporated into other devices with eye imaging capabilities. The device can be provided as an in-home screening device that can be used by a patient to determine if they should see a professional for further evaluation.

Figure 23:
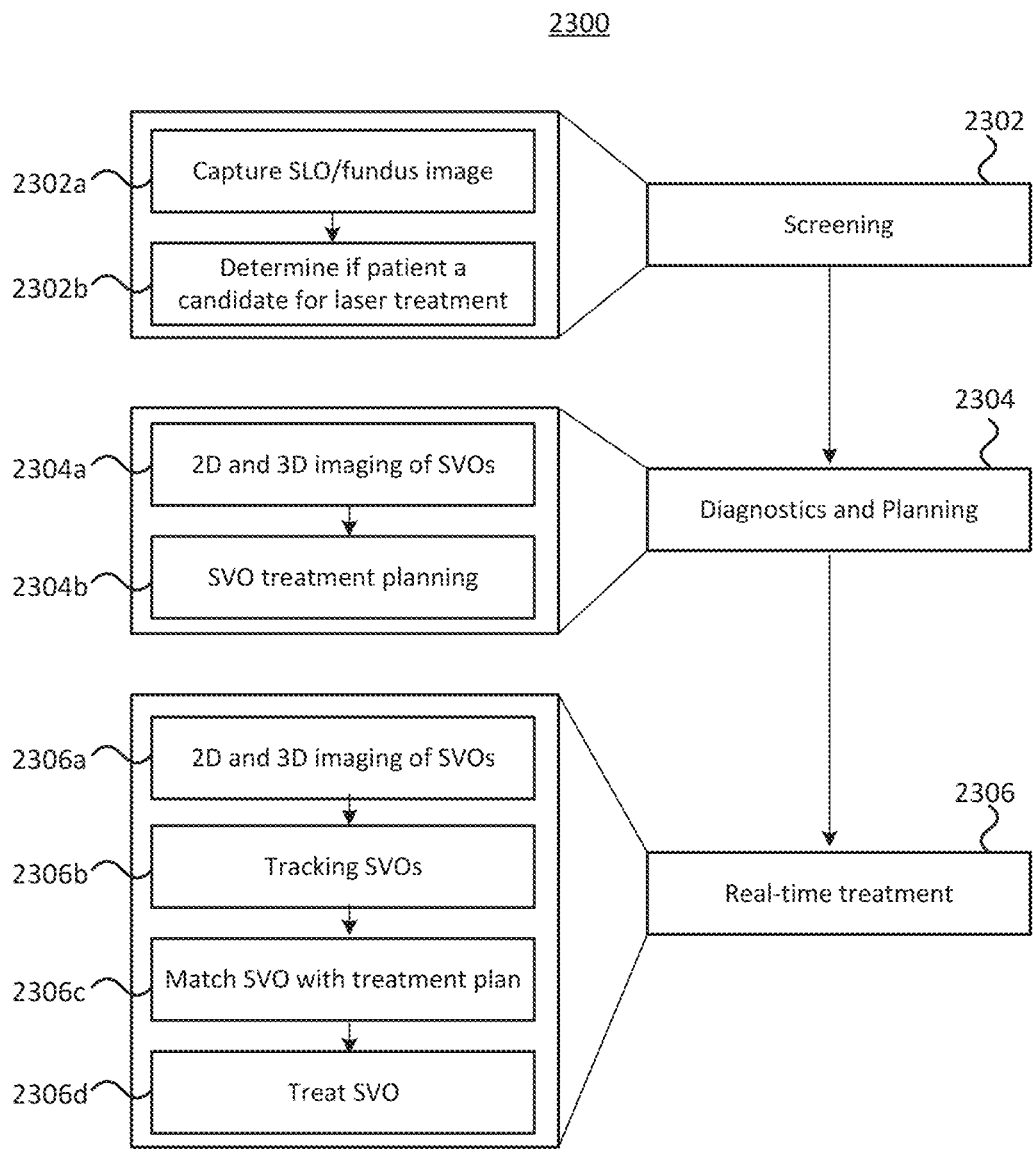
FIG. 23 depicts a method of treating a patient with floaters.

FIG. 23 depicts a method for treating a patient with floaters. The method 2300 can be performed using a single imaging and treatment device or can be done using multiple devices. The method includes an initial screening of the patient (2302) in order to determine if the patient is a good candidate for further treatment. The screening can be performed by the patient themselves using a low cost screening device that only provides basic imaging required to classify the patient as a good candidate or not. The low cost screening device can be provided, for example, as a headset or goggles that the patient puts on and captures a 2D image of the eye (2302a) for example an SLO device, a fundus camera, a slit lamp or other similar imaging device. The low cost device can implement a trained ML model to process the captured images as described above, or the device can capture the images and transmit them for further processing and classification by one or more remote devices. The model can use the images as well as other possible information such as qualitative information provided by the patient. Additional information can be extracted from the images and provided to the trained models, For example a depth of an SVO can be estimated based on relative movement of different SVOs. The classification can identify SVOs within the images or can simply classify the patient as a good candidate for further treatment (2302b). If the screening determines that the patient is a good candidate for further treatment, the patient can be referred to a professional with appropriate devices to further diagnose and/or treat the patient.

The patient can see a professional for further diagnosis and treatment planning (2304). The diagnosis and planning can be provided by a device that includes higher quality imaging devices compared to the screening device. A diagnosis device can have multiple imaging modalities including, for example an SLO imager, an OCT imager such as a swept source OCT that can provide high resolution scanning of the eye, and possibly other imaging devices. Although described as being a diagnosis device, it can also be used for screening as described above. The diagnosis can be performed by capturing 2D and 3D image data of the patient (2304a). The imaging of the patient and the SVOs can capture high resolution images of the SVOs. The captured image data can be processed in non-real-time in order to improve the quality of the images. The processing can including multiple images, possibly from different imaging systems together to generate 3D information about the SVOs.

The 2D and 3D imaging of the SVOs can allow the individual SVOs to be characterized such as their size, opacity, severity, density etc. The device can include additional imaging modalities or sensors such as an aberrometer that can be used in characterizing individual SVOs. During the 2D and 3D diagnostic imaging, the patient can be directed to move their eyes, either by asking the patient, or by adjusting a gaze target and having the patient follow the moving gaze target. The eye movement can help ensure, or at least increase the probability, that all floaters are moved through the field of view of the imaging devices. Further, qualitative information from the patient can be collected and correlated with one or more floaters in the patient's sight. The floaters can be tracked so that when a patient provides qualitative feedback, such as a severity of the floater, it can be correlated with one or more SVOs. The patient can be presented with one or more visuals such as text or graphics to help in providing the qualitative feedback.

The individual SVOs can be identified as being suitable for laser treatment or not based on the characteristics of the SVOs. For the SVOs that are determined to be suitable for laser treatment, dynamic treatment plans can be established by treatment planning (2304b). The dynamic treatment planning can be done manually by a professional explicitly defining all of the parameters for treating an SVO. Alternatively, the planning can be automated or partially automated with the system determining treatment parameters for the SVO. The dynamic treatment plan can determine a scan path, containment patterns, and laser parameters for treating the SVO. The laser parameters can take into account the characteristics of the floater such as its density, opacity. The dynamic treatment plan for a particular SVO can also specify how the SVO treatment should proceed. For example, as the SVO is treated, it can be reduced to multiple smaller SVOs and the treatment plan can provide parameters defining how to automatically treat such SVOs. For example, the treatment plan can specify a maximum size of the reduced SVO that can be treated automatically. For larger SVOs, a further treatment plan can need to be determined and approved. This additional planning and approval can be done while the patient is being treated.

The dynamic planning process segments the floater, possibly into a plurality of voxels as described above, in order to define a contour of the SVO. The segmentation process can be done using a trained ML model. The process can be fully automated, or can allow a professional to provide input in order to adjust an initial segmentation. When the professional updates an initial segmentation, the updated segmentation can be used to retrain the ML model. Once an SVO is segmented, a target volume enclosing the SVO can be defined which in turn can be used for defining scan patterns, such as described with reference to FIG. 17B. Alternatively, the scan pattern can be defined based on the surface of the SVO. If the scan pattern is defined based on a surface of the SVO, it can need to be dynamically updated once the initial surface is treated in order to determine the contours of the new surface.

Once generated, the treatment plan can be stored in association with image data of the SVO. The storage can be provided on the device or can be stored on one or more remote devices including in cloud-based storage. The treatment plan can be carried out in a real-time treatment process (2306). The real-time treatment (2306) can be performed by a treatment device. The treatment device can download or otherwise accessing a previously prepared treatment plan for the patient. The treatment device can be similar to the diagnostic device but further includes at least one treatment laser. It will be appreciated that the treatment device could be used as the diagnostic device as well as the screening device. The diagnostic and planning can be done separately from the treatment or they can both be done during the same visit to the professional.

During the real-time treatment, 2D and 3D imaging is performed (2306a). SVOs are tracked within the captured images (2306b). As an SVO is tracked it is matched to a treatment plan for the SVO (2306c) and the SVO treated according to the plan. While detecting floaters in real time, the 2D and/or 3D images of each detected floater is compared with the images of known floaters, which each have specific identifiers linked to the floater treatment plan. The treatment plan can be overlaid onto the live image of the floater displayed on the GUI. A registration step between the treatment plan to the new orientation of the floater takes place. This can involve capturing the real time 3D image of the floater and comparing with the previously stored 3D image of the floater in the treatment plan. This comparison can be done using 3D registration based on matching 3D keypoints consisting of feature descriptors and then calculating a suitable 3D coordinate transformation from the previously stored 3D floater image to the real time 3D floater image.

The real-time treatment of the SVOs can employ one or more of the safety techniques described above. For example, various different zones can be defined within which treatment can be considered safe or not. The zones can be dynamically determined and treatment within a zone can be verified prior to performing the laser treatment or pulse. The safe zones can be adjusted dynamically during the treatment process, for example based on an amount of pulses delivered to the retina. For example, once a certain amount of pulses or power has been delivered to the same area of the retina, that area can be dynamically identified as an unsafe region.

New floaters resulting from the breaking down of large floaters can be detected and receive their own identifiers that can be associated with the original SVO in order to provide a hierarchy or family tree of SVOs. During treatment, a "dynamic" treatment planning mode can be applied to these new floaters. As described, the treatment plan can specify how to treat new floaters. The professional can decide if each new floater should be treated as well as possibly selecting a desired treatment location in the 3D floater image. The treatment of an SVO can continue until it is determined that it has been sufficiently treated. The treatment plan for an SVO can include one or more parameters that specify when to stop treatment such as a shadow size on the retina or a volume of the floater. For example, the treatment plan can specify that once all of the particles of the floater are below a certain threshold, such as less than 1 mm, less than 0.5 mm or less than 0.1 mm, treatment of the SVO can be stopped. Once the there are no more SVOs that can be safely treated, the real-time treatment can be completed.

As described above, an imaging and treatment device can be used in both an imaging mode and treatment mode. During imaging, the captured image data does not need to be processed in real time and as such high quality image processing can be applied. Additionally, a single SVO can be imaged multiple times as it moves within the eye, and the multiple images combined into a single high quality 3D representation of the SVO. During the imaging process used for the diagnosis and planning the professional can be presented with both a static view of the patient's eye and the live views captured by the different imaging devices. The professional can be able to zoom in and out of certain locations in the images. The zoom in and zoom out functionality can be provided by capturing a high resolution image and then expanding an area of the high resolution image. During treatment, it may not be necessary to image the SVO in as complete detail and as such a lower resolution imaging with a larger field of view can be used for the OCT imaging system. For example, the scan lines of the OCT imaging device can be spaced further apart in order to create the OCT image at a lower resolution. Following treatment, the patient can be re-evaluated in order to determine if the treatment was successful. The evaluation can use the imaging systems to identify any remaining SVOs, an aberrometer to determine if the aberrations have improved, or more qualitative assessments of the patient.

It will be appreciated by one of ordinary skill in the art that the system and components shown in FIGS. 1-23 can include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Although certain components and steps have been described, it is contemplated that individually described components, as well as steps, can be combined together into fewer components or steps or the steps can be performed sequentially, non-sequentially or concurrently. Further, although described above as occurring in a particular order, one of ordinary skill in the art having regard to the current teachings will appreciate that the particular order of certain steps relative to other steps can be changed. Similarly, individual components or steps can be provided by a plurality of components or steps. One of ordinary skill in the art having regard to the current teachings will appreciate that the components and processes described herein can be provided by various combinations of software, firmware and/or hardware, other than the specific implementations described herein as illustrative examples.

The techniques of various embodiments can be implemented using software, hardware and/or a combination of software and hardware. Various embodiments are directed to apparatus, e.g. a node which can be used in a communications system or data storage system. Various embodiments are also directed to non-transitory machine, e.g., computer, readable medium, e.g., ROM, RAM, CDs, hard discs, etc., which include machine readable instructions for controlling a machine, e.g., processor to implement one, more or all of the steps of the described method or methods.

Some embodiments are directed to a computer program product comprising a computer-readable medium comprising code for causing a computer, or multiple computers, to implement various functions, steps, acts and/or operations, e.g. one or more or all of the steps described above. Depending on the embodiment, the computer program product can, and sometimes does, include different code for each step to be performed. Thus, the computer program product may, and sometimes does, include code for each individual step of a method, e.g., a method of operating a communications device, e.g., a wireless terminal or node. The code can be in the form of machine, e.g., computer, executable instructions stored on a computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the method(s) described herein. The processor can be for use in, e.g., a communications device or other device described in the present application.

Numerous additional variations on the methods and apparatus of the various embodiments described above will be apparent to those skilled in the art in view of the above description. Such variations are to be considered within the scope.

What is claimed is:

1. A system for use in treatment of floaters in an eye of a patient comprising:
   a first imaging system for capturing real-time 2-dimensional (2D) images of the patient's eye;
   an optical coherence tomography (OCT) imaging system for capturing depth information of the patient's eye along a plurality of scan lines;

a laser treatment system for focusing and firing a treatment laser at a treatment target location within a volume of the patient's eye; and a controller for controlling the first imaging system and the laser treatment system, the controller configured to:
detect a floater in at least one of the 2D images captured by the first imaging system using a machine learning (ML) algorithm;
capture depth information, using an OCT imaging system, along scan lines at a location within the patient's eye based on a location of the detected floater in the at least one 2D images;
determine a depth of the floater based on the depth information captured by the OCT imaging system along the scan lines; and
track a position of the detected floater in a 3-dimensional (3D) volume of the patient's eye using X-Y position data from the first imaging system and Z position data from the OCT imaging system.

2. The system of claim 1, wherein the first imaging system comprises a scanning laser ophthalmoscopy imaging system.

3. The system of claim 2, wherein the treatment laser comprises a femtosecond laser.

4. The system of claim 3, wherein detecting the floater further comprises detecting and removing non-floater features of the eye from the image prior to using the ML algorithm, the non-floater features detected using at least one of:
a machine learning image classification technique; and
an object detection technique.

5. The system of claim 4, wherein tracking the position of the detected floater comprises stabilizing images subsequently captured by the first imaging system.

6. The system of claim 4, wherein the controller determines one or more of:
a number of floaters;
a surface area of floaters;
a volume of floaters;
a location of floaters;
an opacity of floaters;
a refractive index of floaters;
a speed of movement of floaters;
a direction of movement of floaters;
a concentration of floaters;
a shape of floaters; and
a group of connected basic structures defining a shape of floaters.

7. The system of claim 3, wherein the controller is further configured to predict a future position of the detected floater.

8. The system of claim 7, further comprising a gaze display that is controlled in order to, at least one of:
cause a patient to move their eye in a manner to affect a motion of a floater; or
determine a subjective impact of a floater on a patient's vision.

9. The system of claim 2, wherein ML algorithm uses large kernels for object detection.

10. The system of claim 9, wherein the large kernels have dimensions of at least 8×8.

11. The system of claim 1, wherein detecting the floater uses a convolutional neural network (CNN) that takes as input a sequence of a number (M) of image frames captured by the first imaging system and determines a sequence of M floater detection masks corresponding to floater locations in each image frame of the input sequence.

12. The system of claim 11, wherein detecting the floater comprises:
applying the CNN to a plurality of input sequences of M image frames, each of the plurality of input sequences including a frame of interest to provide a plurality of floater mask sequences each including a floater detection mask for the frame of interest; and
summing the floater detection masks for the frame of interest from each of the plurality of floater mask sequences.

13. The system of claim 1, wherein focusing the treatment laser comprises:
focusing the laser according to a treatment pattern determined for at least a portion of the detected floater, the treatment pattern providing a volume of laser pulses to the floater.

14. The system of claim 13, wherein the controller is further configured to:
focus the treatment laser of the laser treatment system at the tracked position and depth of the detected floater for subsequent firing of treatment laser to treat the floater.

15. The system of claim 14, wherein treatment of the floater by the treatment laser eliminates at least a portion of the floater.

16. The system of claim 14, wherein the controller monitors safe and unsafe locations to focus the treatment laser within the patient's eye.

17. The system of claim 14, wherein the first imaging system, the OCT imaging system, and the laser treatment system are co-registered.

18. A method for use in treatment of a floater, the method comprising:
detecting, using a machine learning (ML) algorithm, a floater in at least one 2-dimensional (2D) image captured of a patient's eye;
capturing depth information, using an OCT imaging system, along scan lines at a location within the patient's eye based on a location of the detected floater in the 2D image;
determining a depth of the floater based on the depth information captured by the OCT imaging system along the scan lines;
tracking a position of the detected floater in a 3-dimensional (3D) volume of the patient's eye using X-Y position data from a first imaging system and Z position data from the OCT imaging system.

19. The method of claim 18, wherein detecting the floater is performed at a controller of an imaging system.

20. The method of claim 18, wherein detecting the floater is performed at remote server separate from a controller of an imaging system, and subsequently captured images are buffered.

21. The method of claim 18, wherein tracking the position of the detected floater comprises stabilizing images subsequently captured by the OCT imaging system.

22. The method of claim 21, wherein stabilizing the image comprises tracking retina movement in order to determine movement to be stabilized.

23. The method of claim 18, further comprising: determining one or more of:
a number of floaters;
a surface area of floaters;
a volume of floaters;
a location of floaters;
an opacity of floaters;
a refractive index of floaters;
a speed of movement of floaters;

a direction of movement of floaters; and a concentration of floaters;

a shape of floaters; and a group of connected basic structures defining a shape of floaters.

24. The method of claim 18, wherein detecting the floater uses a convolutional neural network (CNN) that takes as input a sequence of a number (M) of image frames captured by the OCT imaging system and determines a sequence of M floater detection masks corresponding to floater locations in each image frame of the input sequence.

25. The method of claim 24, wherein detecting the floater comprises:

applying the CNN to a plurality of input sequences of M image frames, each of the plurality of input sequences including a frame of interest to provide a plurality of floater mask sequences each including a floater detection mask for the frame of interest; and summing the floater detection masks for the frame of interest from each of the plurality of floater mask sequences.

26. The method of claim 18, further comprising:

focusing a treatment laser of a laser treatment system at the tracked position and depth of the detected floater for subsequent firing of treatment laser to eliminate at least a portion of the floater.

27. The method of claim 26, further comprising monitoring safe and unsafe locations to focus the treatment laser within the patient's eye.

28. The method of claim 27, further comprising co-registering an imaging system capturing the 2D image, the OCT imaging system and the laser treatment system.

29. The method of claim 18, wherein the ML algorithm uses large kernels for object detection that have dimensions of at least 8×8.

30. A non-transitory computer readable medium having stored thereon instructions, which when executed by a processor of a computing device, configure the device to provide a method for use in treatment of a floater, the method comprising:

detecting a floater in a 2-dimensional (2D) image captured of a patient's eye;

capturing depth information, using an OCT imaging system, along scan lines at a location within the patient's eye based on a location of the detected floater in the 2D image;

determining a depth of the floater based on the depth information captured by the OCT imaging system along the scan lines; and tracking a position of the detected floater in a 3-dimensional (3D) volume of the patient's eye using X-Y position data from a first imaging system and Z position data from the OCT imaging system.

* * * * *